US010478482B2

(12) United States Patent
Maeurer

(10) Patent No.: US 10,478,482 B2
(45) Date of Patent: Nov. 19, 2019

(54) VACCINES FOR PREVENTION AND TREATMENT OF TUBERCULOSIS

(71) Applicant: Markus Maeurer, Akersberga (SE)

(72) Inventor: Markus Maeurer, Akersberga (SE)

(73) Assignee: ALARUM DEVELOPMENT LTD, Limassol (CY)

( * ) Notice: Subject to any disclaimer, the term of this patent is extended or adjusted under 35 U.S.C. 154(b) by 0 days.

(21) Appl. No.: 16/285,353

(22) Filed: Feb. 26, 2019

(65) Prior Publication Data

US 2019/0175715 A1 Jun. 13, 2019

Related U.S. Application Data

(60) Division of application No. 15/645,760, filed on Jul. 10, 2017, which is a continuation of application No. 14/009,931, filed as application No. PCT/EP2012/056558 on Apr. 11, 2012, now abandoned.

(60) Provisional application No. 61/477,457, filed on Apr. 20, 2011.

(30) Foreign Application Priority Data

Apr. 11, 2011 (SE) ...................................... 1130027

(51) Int. Cl.
| | |
|---|---|
| *A61K 39/04* | (2006.01) |
| *A61K 39/00* | (2006.01) |
| *C07K 14/35* | (2006.01) |
| *C12Q 1/48* | (2006.01) |
| *G01N 33/569* | (2006.01) |
| *C12N 15/117* | (2010.01) |

(52) U.S. Cl.
CPC .............. *A61K 39/04* (2013.01); *C07K 14/35* (2013.01); *C12N 15/117* (2013.01); *C12Q 1/48* (2013.01); *A61K 2039/522* (2013.01)

(58) Field of Classification Search
CPC .. A61K 39/04; A61K 2039/522; C07K 14/35; C12N 15/117; C12Q 1/48; G01N 2469/20; G01N 2800/52; G01N 33/5695; G01N 33/56977; Y10S 530/802; Y10S 530/806; Y10S 530/825
See application file for complete search history.

(56) References Cited

U.S. PATENT DOCUMENTS

| 6,583,266 B1 | 6/2003 | Smith et al. | |
|---|---|---|---|
| 2007/0264286 A1* | 11/2007 | Liu | C12N 9/0016 424/248.1 |
| 2009/0136534 A1 | 5/2009 | Shafferman et al. | |

FOREIGN PATENT DOCUMENTS

| WO | 97/23624 A2 | 7/1997 |
|---|---|---|
| WO | 03/089462 A2 | 10/2003 |
| WO | 2006/102767 A1 | 10/2006 |

OTHER PUBLICATIONS

Rao et al. International J. Infect. Dis. 56: 274-282, 2017.*
Written opinion and International Search report dated Mar. 8, 2012 in parent PCT/EP2012/056558.
Flynn et al., "Tuberculosis: latency and reactivation", Infect Immun, 2001, vol. 69, No. 7, pp. 4195-4201.
Munoz-Elias et al., "Replication dynamics of *Mycobacterium tuberculosis* in chronically infected mice", Infect Immun, 2005, vol. 73, No. 1, pp. 546-551.
Voskuil et al., "Inhibition of respiration by nitric oxide induces a *Mycobacterium tuberculosis* dormancy program", J Exp Med, 2003. vol. 198, No. 5, pp. 705-713.
Lin, M.Y. and T.H. Ottenhoff, :Not to wake a sleeping giant: new insights into host-pathogen interactions identify new targets for vaccination against latent *Mycobacterium tuberculosis* infection, Biol Chem, 2008. vol. 389, No. 5, pp. 497-511.
Endsley et al., "*Mycobacterium bovis* BCG vaccination induces memory CD4 T cells characterized by effector biomarker expression and antimycobacterial activity", Vaccine 2007. vol. 25, pp. 8384-8394.
Kettaneh et al., "Human leukocyte antigens and susceptibility to tuberculosis: a metaanalysis of case-control studies", Int. J. Tuberc. Lung Dis. 2006. vol. 10, pp. 717-725.
Kim et al., "Association of HLA-DR and HLA-DQ genes with susceptibility to pulmonary tuberculosis in Koreans: preliminary evidence of associations with drug resistance, disease severity, and disease recurrence", Hum. Immunol. 2005. vol. 66, pp. 1074-1081.
Lombard et al., "Association of HLA-DR, -DQ, and vitamin D receptor alleles and haplotypes with tuberculosis in the Venda of South Africa", Hum. Immunol., 2006, vol. 67, pp. 643-654.
Teran-Escandon et al., "Human leukocyte antigen-associated susceptibility to pulmonary tuberculosis: molecular analysis of class II alleles by DNA amplification and oligonucleotide hybridization in Mexican patients", Chest 1999, vol. 115, pp. 428-433.
"Developing an epitope-driven tuberculosis (TB) vaccine", Vaccine 2005, vol. 23, pp. 2121-2131.
Blythe et al., "An analysis of the epitope knowledge related to mycobacteria". Immunome Res. 2007, vol. 3, p. 10.
"Peptide microarray-based identification of *Mycobacterium tuberculosis* epitope binding to HLA-DRBV0101, DRB1*1501 and DRB1*0401", Clin Vacc Immunol 2010, vol. 17, pp. 168-175.

(Continued)

*Primary Examiner* — Sarvamangala Devi
(74) *Attorney, Agent, or Firm* — Jeffrey S. Melcher; Melcher Patent Law PLLC

(57) ABSTRACT

The present invention provides new immunological compositions and vaccines comprising selected *M. tuberculosis* antigens and antigenic peptides as well as nucleic acids encoding said antigens for use in the prevention, prophylaxis and treatment of mycobacterial infection, especially tuberculosis. In particular the invention provides recombinant BCG based vaccines in which one or more of the selected *M. tuberculosis* antigens are over expressed. The invention further provides isolated peptides for use in methods for diagnosing, characterizing, or classifying mycobacterial infections.

2 Claims, 16 Drawing Sheets

Specification includes a Sequence Listing.

(56) References Cited

OTHER PUBLICATIONS

"Cyclopropane-fatty-acyl-phospholipid synthase ufaA1", XP002676928, retrieved from EBI accession No. UNUPROT: E2T8F4, Jan. 11, 2011.

"Putative uncharacterized protein", XP002676929, retrieved from EBI accession No. UNIPROT:D7EVV0, Aug. 10, 2010.

Guinvarc'h et al., "Identification of new inhibitors of *E. coli* cyclopropane fatty acid synthase using a colorimetric assay", Biochimica et Biophysica Acta (BBA)—PRoteins & Protemics, Elsevier, Netherlands, vol. 1764, No. 8, Aug. 1, 2006, pp. 1381-1388.

Gaseitiwe et al., "Pattern Recognition in Pulmonary Tuberculosis Defined by High Content Peptide Microarray Chip Analysis Representing 61 Proteins from N. tuberculosis", Plos One, vol. 3, No. 12, E3840, Dec. 2008.

Ahmed et al., "Pattern recognition and cellular immune responses to novel *Mycobacterium tuberculosis*-antigens in individuals from Belarus", BMC Intfectious Diseases 2012 LNKD-OUBMED:22336002, vol. 12, Feb. 14, 2012, p. 41.

Horwitz et al., "Recombinant bacillus Calmette-Guerin (BCG) vaccines expressing the *Mycobacterium tuberculosis* 30-kDa major secretory protein induce greater protective immunity against tuberculosis than conventional BCG vaccines in a highly susceptible animal model", Proceedings of the National Academy of Sciences, vol. 97, No. 25, Dec. 5, 2000, pp. 13853-13858.

Horwitz et al., "Protective immunity against tuberculosis induced by vaccination with major extracellular proteins of *Mycobacterium tuberculosis*", Proceedings of the National Academy of Sciences, vol. 92, No. 1, Feb. 1, 1995, pp. 1530-1534.

Sander et al., "Translational mini-review series on vaccines: Development and evaluation of improved vaccines against tuberculosis", Clinical and Experimental Immunology, Wiley-Blackwell Publishing Ltd, GB, vol. 147, No. 3, Mar. 1, 2007, pp. 401-411.

Girard et al., "A review of vaccine research and development: Tuberculosis", Vaccine, Eslevier Ltd, GB, vol. 23, No. 50, Dec. 30, 2005, pp. 5725-5731.

Orme et al., "Preclinical testing of new vaccines for tuberculosis: A comprehensive review", Vaccine, Elsevier Ltd, GB, vol. 24, No. 1, Jan. 9, 2006, pp. 2-19.

Rosas-Magallanes et al., "Signature-tagged transposon mutagenesis identifies novel *Mycobacterium tuberculosis* genes involved in the parasitism of human macrophages", Infection and Immunity, vol. 75, No. 1, Jan. 2007, pp. 504-507.

Perez et al., "Characterization of three glycosyltransferases involved in the biosynthesis of the phenolic glycolipid antigens from the *Mycobacterium tuberculosis* complex", Journal of Biological Chemistry, vol. 279, No. 41, Oct. 8, 2004, pp. 42574-42583.

Onwueme et al., "The dimycocerosate ester polyketide virulence factors of mycobacteria", Progress in Lipid Research, Pergamon Press, Paris, FR, vol. 44, No. 5, Sep. 1, 2005, pp. 259-302.

Tam et al., "Recent advances in mycobacterial cell wall glycan biosynthesis", Current Opinion on Chemical Biology, Current Biology Ltd, London, GB, vol. 13, No. 5-6, Dec. 1, 2009, pp. 618-625.

Malaga et al., "Deciphering the Genetic Bases of the Structural Diversity of Phenolic Glycolipids in Strains of the *Mycobacterium tuberculosis* Complex", Journal of Biological Chemistry, vol. 283, No. 22, Jan. 1, 2008, pp. 15177-15184.

Kirksey et al., "Spontaneous Phthiocerol Dimycocerosate-Deficient Variants of *Mycobacterium tuberculosis* Are Susceptible to Gamma Interferon-Mediated Immunity", Infection and Immunity, vol. 79, No. 7, Jul. 2011, pp. 2829-2838.

\* cited by examiner

Figure 12

SEQUENCE LISTING

```
<160> NUMBER OF SEQ ID NOS: 118

<210> SEQ ID NO 1
<211> LENGTH: 427
<212> TYPE: PRT
<213> ORGANISM: Mycobacterium tuberculosis

<400> SEQUENCE: 1

Met Thr Val Glu Thr Ser Gln Thr Pro Ser Ala Ala Ile Asp Ser Asp
1               5                   10                  15

Arg Trp Pro Ala Val Ala Lys Val Pro Arg Gly Pro Leu Ala Ala Ala
            20                  25                  30

Ser Ala Ala Ile Ala Asn Arg Leu Leu Arg Arg Thr Ala Thr His Leu
        35                  40                  45

Pro Leu Arg Leu Val Tyr Ser Asp Gly Thr Ala Thr Gly Ala Ala Asp
    50                  55                  60

Pro Arg Ala Pro Ser Leu Phe Ile His Arg Pro Asp Ala Leu Ala Arg
65                  70                  75                  80

Arg Ile Gly Arg His Gly Leu Ile Gly Phe Gly Glu Ser Tyr Met Ala
                85                  90                  95

Gly Glu Trp Ser Ser Lys Glu Leu Thr Arg Val Leu Thr Val Leu Ala
            100                 105                 110

Gly Ser Val Asp Glu Leu Val Pro Arg Ser Leu His Trp Leu Arg Pro
        115                 120                 125

Ile Thr Pro Thr Phe Arg Pro Ser Trp Pro Asp His Ser Arg Asp Gln
    130                 135                 140

Ala Arg Arg Asn Ile Ala Val His Tyr Asp Leu Ser Asn Asp Leu Phe
145                 150                 155                 160

Ala Ala Phe Leu Asp Glu Thr Met Thr Tyr Ser Cys Ala Met Phe Thr
                165                 170                 175

Asp Leu Leu Ala Gln Pro Thr Pro Ala Trp Thr Glu Leu Ala Ala Ala
            180                 185                 190

Gln Arg Arg Lys Ile Asp Arg Leu Leu Asp Val Ala Gly Val Gln Gln
```

```
            195                 200                 205
Gly Ser His Val Leu Glu Ile Gly Thr Gly Trp Gly Glu Leu Cys Ile
210                 215                 220

Arg Ala Ala Arg Gly Ala His Ile Arg Ser Val Thr Leu Ser Val
225                 230                 235                 240

Glu Gln Gln Arg Leu Ala Arg Gln Arg Val Ala Ala Gly Phe Gly
                    245                 250                 255

His Arg Val Glu Ile Asp Leu Cys Asp Tyr Arg Asp Val Asp Gly Gln
                260                 265                 270

Tyr Asp Ser Val Val Ser Val Glu Met Ile Glu Ala Val Gly Tyr Arg
                275                 280                 285

Ser Trp Pro Arg Tyr Phe Ala Ala Leu Glu Gln Leu Val Arg Pro Gly
                290                 295                 300

Gly Pro Val Ala Ile Gln Ala Ile Thr Met Pro His His Arg Met Leu
305                 310                 315                 320

Ala Thr Arg His Thr Gln Thr Trp Ile Gln Lys Tyr Ile Phe Pro Gly
                    325                 330                 335

Gly Leu Leu Pro Ser Thr Gln Ala Ile Ile Asp Ile Thr Gly Gln His
                340                 345                 350

Thr Gly Leu Arg Ile Val Asp Ala Ala Ser Leu Arg Pro His Tyr Ala
                355                 360                 365

Glu Thr Leu Arg Leu Trp Arg Glu Arg Phe Met Gln Arg Arg Asp Gly
370                 375                 380

Leu Ala His Leu Gly Phe Asp Glu Val Phe Ala Arg Met Trp Glu Leu
385                 390                 395                 400

Tyr Leu Ala Tyr Ser Glu Ala Gly Phe Arg Ser Gly Tyr Leu Asp Val
                    405                 410                 415

Tyr Gln Trp Thr Leu Ile Arg Glu Gly Pro Pro
                420                 425

<210> SEQ ID NO 2
<211> LENGTH: 428
<212> TYPE: PRT
<213> ORGANISM: Mycobacterium tuberculosis

<400> SEQUENCE: 2

Met Glu Glu Thr Ser Val Ala Gly Asp Pro Gly Pro Asp Ala Gly Thr
1               5                   10                  15

Ser Thr Ala Pro Asn Ala Ala Pro Glu Pro Val Ala Arg Arg Gln Arg
                20                  25                  30

Ile Leu Phe Val Gly Glu Ala Ala Thr Leu Ala His Val Val Arg Pro
                35                  40                  45

Phe Val Leu Ala Arg Ser Leu Asp Pro Ser Arg Tyr Glu Val His Phe
            50                  55                  60

Ala Cys Asp Pro Arg Phe Asn Lys Leu Leu Gly Pro Leu Pro Phe Pro
65              70                  75                  80

His His Pro Ile His Thr Val Pro Ser Glu Val Leu Leu Lys Ile
                    85                  90                  95

Ala Gln Gly Arg Leu Phe Tyr Asn Thr Arg Thr Leu Arg Lys Tyr Ile
                100                 105                 110

Ala Ala Asp Arg Lys Ile Leu Asn Glu Ile Ala Pro Asp Val Val Val
            115                 120                 125

Gly Asp Asn Arg Leu Ser Leu Ser Val Ser Ala Arg Leu Ala Gly Ile
    130                 135                 140
```

Pro Tyr Ile Ala Ile Ala Asn Ala Tyr Trp Ser Pro Gln Ala Arg Arg
145                 150                 155                 160

Arg Phe Pro Leu Pro Asp Val Pro Trp Thr Arg Phe Phe Gly Val Arg
            165                 170                 175

Pro Val Ser Ile Leu Tyr Arg Leu Tyr Arg Pro Leu Ile Phe Ala Leu
        180                 185                 190

Tyr Cys Leu Pro Leu Asn Trp Leu Arg Arg Lys His Gly Leu Ser Ser
    195                 200                 205

Leu Gly Trp Asp Leu Cys Arg Ile Phe Thr Asp Gly Asp Tyr Thr Leu
210                 215                 220

Tyr Ala Asp Val Pro Glu Leu Val Pro Thr Tyr Asn Leu Pro Ala Asn
225                 230                 235                 240

His Arg Tyr Leu Gly Pro Val Leu Trp Ser Pro Asp Val Lys Pro Pro
            245                 250                 255

Thr Trp Trp His Ser Leu Pro Thr Asp Arg Pro Ile Ile Tyr Ala Thr
            260                 265                 270

Leu Gly Ser Ser Gly Gly Lys Asn Leu Leu Gln Val Val Leu Asn Ala
        275                 280                 285

Leu Ala Asp Leu Pro Val Thr Val Ile Ala Thr Ala Gly Arg Asn
290                 295                 300

His Leu Lys Asn Val Pro Ala Asn Ala Phe Val Ala Asp Tyr Leu Pro
305                 310                 315                 320

Gly Glu Ala Ala Ala Ala Arg Ser Ala Val Val Leu Cys Asn Gly Gly
                325                 330                 335

Ser Pro Thr Thr Gln Gln Ala Leu Ala Ala Gly Val Pro Val Ile Gly
            340                 345                 350

Leu Pro Ser Asn Met Asp Gln His Leu Asn Met Glu Ala Leu Glu Arg
        355                 360                 365

Ala Gly Ala Gly Val Leu Leu Arg Thr Glu Arg Leu Asn Thr Glu Gly
370                 375                 380

Val Ala Ala Val Lys Gln Val Leu Ser Gly Ala Glu Phe Arg Gln
385                 390                 395                 400

Ala Ala Arg Arg Leu Ala Glu Ala Phe Gly Pro Asp Phe Ala Gly Phe
            405                 410                 415

Pro Gln His Ile Glu Ser Ala Leu Arg Leu Val Cys
        420                 425

<210> SEQ ID NO 3
<211> LENGTH: 275
<212> TYPE: PRT
<213> ORGANISM: Mycobacterium tuberculosis

<400> SEQUENCE: 3

Met Val Gln Thr Lys Arg Tyr Ala Gly Leu Thr Ala Ala Asn Thr Lys
1               5                   10                  15

Lys Val Ala Met Ala Ala Pro Met Phe Ser Ile Ile Pro Thr Leu
            20                  25                  30

Asn Val Ala Ala Val Leu Pro Ala Cys Leu Asp Ser Ile Ala Arg Gln
            35                  40                  45

Thr Cys Gly Asp Phe Glu Leu Val Leu Val Asp Gly Gly Ser Thr Asp
        50                  55                  60

Glu Thr Leu Asp Ile Ala Asn Ile Phe Ala Pro Asn Leu Gly Glu Arg
65                  70                  75                  80

Leu Ile Ile His Arg Asp Thr Asp Gln Gly Val Tyr Asp Ala Met Asn
                85                  90                  95

```
Arg Gly Val Asp Leu Ala Thr Gly Thr Trp Leu Leu Phe Leu Gly Ala
            100                 105                 110

Asp Asp Ser Leu Tyr Glu Ala Asp Thr Leu Ala Arg Val Ala Ala Phe
            115                 120                 125

Ile Gly Glu His Glu Pro Ser Asp Leu Val Tyr Gly Asp Val Ile Met
        130                 135                 140

Arg Ser Thr Asn Phe Arg Trp Gly Gly Ala Phe Asp Leu Asp Arg Leu
145                 150                 155                 160

Leu Phe Lys Arg Asn Ile Cys His Gln Ala Ile Phe Tyr Arg Arg Gly
                165                 170                 175

Leu Phe Gly Thr Ile Gly Pro Tyr Asn Leu Arg Tyr Arg Val Leu Ala
            180                 185                 190

Asp Trp Asp Phe Asn Ile Arg Cys Phe Ser Asn Pro Ala Leu Val Thr
            195                 200                 205

Arg Tyr Met His Val Val Val Ala Ser Tyr Asn Glu Phe Gly Gly Leu
        210                 215                 220

Ser Asn Thr Ile Val Asp Lys Glu Phe Leu Lys Arg Leu Pro Met Ser
225                 230                 235                 240

Thr Arg Leu Gly Ile Arg Leu Val Ile Val Leu Val Arg Arg Trp Pro
                245                 250                 255

Lys Val Ile Ser Arg Ala Met Val Met Arg Thr Val Ile Ser Trp Arg
                260                 265                 270

Arg Arg Arg
        275

<210> SEQ ID NO 4
<211> LENGTH: 9
<212> TYPE: PRT
<213> ORGANISM: Mycobacterium tuberculosis

<400> SEQUENCE: 4

Val Leu Ala Gly Ser Val Asp Glu Leu
1               5

<210> SEQ ID NO 5
<211> LENGTH: 9
<212> TYPE: PRT
<213> ORGANISM: Mycobacterium tuberculosis

<400> SEQUENCE: 5

Lys Tyr Ile Phe Pro Gly Gly Leu Leu
1               5

<210> SEQ ID NO 6
<211> LENGTH: 9
<212> TYPE: PRT
<213> ORGANISM: Mycobacterium tuberculosis

<400> SEQUENCE: 6

Arg Met Trp Glu Leu Tyr Leu Ala Tyr
1               5

<210> SEQ ID NO 7
<211> LENGTH: 9
<212> TYPE: PRT
<213> ORGANISM: Mycobacterium tuberculosis

<400> SEQUENCE: 7

Ala Ala Ser Ala Ala Ile Ala Asn Arg
```

```
1               5

<210> SEQ ID NO 8
<211> LENGTH: 9
<212> TYPE: PRT
<213> ORGANISM: Mycobacterium tuberculosis

<400> SEQUENCE: 8

Ala Leu Ala Asp Leu Pro Val Thr Val
1               5

<210> SEQ ID NO 9
<211> LENGTH: 9
<212> TYPE: PRT
<213> ORGANISM: Mycobacterium tuberculosis

<400> SEQUENCE: 9

Lys Tyr Ile Ala Ala Asp Arg Lys Ile
1               5

<210> SEQ ID NO 10
<211> LENGTH: 9
<212> TYPE: PRT
<213> ORGANISM: Mycobacterium tuberculosis

<400> SEQUENCE: 10

Ser Ala Arg Leu Ala Gly Ile Pro Tyr
1               5

<210> SEQ ID NO 11
<211> LENGTH: 9
<212> TYPE: PRT
<213> ORGANISM: Mycobacterium tuberculosis

<400> SEQUENCE: 11

Ala Ala Pro Glu Pro Val Ala Arg Arg
1               5

<210> SEQ ID NO 12
<211> LENGTH: 9
<212> TYPE: PRT
<213> ORGANISM: Mycobacterium tuberculosis

<400> SEQUENCE: 12

Ala Thr Leu Gly Ser Ser Gly Gly Lys
1               5

<210> SEQ ID NO 13
<211> LENGTH: 9
<212> TYPE: PRT
<213> ORGANISM: Mycobacterium tuberculosis

<400> SEQUENCE: 13

Ala Thr Ala Gly Arg Asn His Leu Lys
1               5

<210> SEQ ID NO 14
<211> LENGTH: 9
<212> TYPE: PRT
<213> ORGANISM: Mycobacterium tuberculosis

<400> SEQUENCE: 14

Ser Ile Ile Ile Pro Thr Leu Asn Val
1               5
```

<210> SEQ ID NO 15
<211> LENGTH: 9
<212> TYPE: PRT
<213> ORGANISM: Mycobacterium tuberculosis

<400> SEQUENCE: 15

Pro Tyr Asn Leu Arg Tyr Arg Val Leu
1               5

<210> SEQ ID NO 16
<211> LENGTH: 9
<212> TYPE: PRT
<213> ORGANISM: Mycobacterium tuberculosis

<400> SEQUENCE: 16

Ile Val Leu Val Arg Arg Trp Pro Lys
1               5

<210> SEQ ID NO 17
<211> LENGTH: 9
<212> TYPE: PRT
<213> ORGANISM: Mycobacterium tuberculosis

<400> SEQUENCE: 17

Leu Val Tyr Gly Asp Val Ile Met Arg
1               5

<210> SEQ ID NO 18
<211> LENGTH: 9
<212> TYPE: PRT
<213> ORGANISM: Mycobacterium tuberculosis

<400> SEQUENCE: 18

Ser Asp Arg Trp Pro Ala Val Ala Lys
1               5

<210> SEQ ID NO 19
<211> LENGTH: 9
<212> TYPE: PRT
<213> ORGANISM: Mycobacterium tuberculosis

<400> SEQUENCE: 19

Thr His Leu Pro Leu Arg Leu Val Tyr
1               5

<210> SEQ ID NO 20
<211> LENGTH: 9
<212> TYPE: PRT
<213> ORGANISM: Mycobacterium tuberculosis

<400> SEQUENCE: 20

Gly Leu Ile Gly Phe Gly Glu Ser Tyr
1               5

<210> SEQ ID NO 21
<211> LENGTH: 9
<212> TYPE: PRT
<213> ORGANISM: Mycobacterium tuberculosis

<400> SEQUENCE: 21

Tyr Met Ala Gly Glu Trp Ser Ser Lys
1               5

<210> SEQ ID NO 22

```
<211> LENGTH: 9
<212> TYPE: PRT
<213> ORGANISM: Mycobacterium tuberculosis

<400> SEQUENCE: 22

Ala Arg Arg Asn Ile Ala Val His Tyr
1               5

<210> SEQ ID NO 23
<211> LENGTH: 9
<212> TYPE: PRT
<213> ORGANISM: Mycobacterium tuberculosis

<400> SEQUENCE: 23

Ala Phe Leu Asp Glu Thr Met Thr Tyr
1               5

<210> SEQ ID NO 24
<211> LENGTH: 9
<212> TYPE: PRT
<213> ORGANISM: Mycobacterium tuberculosis

<400> SEQUENCE: 24

Glu Leu Ala Ala Ala Gln Arg Arg Lys
1               5

<210> SEQ ID NO 25
<211> LENGTH: 9
<212> TYPE: PRT
<213> ORGANISM: Mycobacterium tuberculosis

<400> SEQUENCE: 25

Arg Val Glu Ile Asp Leu Cys Asp Tyr
1               5

<210> SEQ ID NO 26
<211> LENGTH: 9
<212> TYPE: PRT
<213> ORGANISM: Mycobacterium tuberculosis

<400> SEQUENCE: 26

Asp Tyr Arg Asp Val Asp Gly Gln Tyr
1               5

<210> SEQ ID NO 27
<211> LENGTH: 9
<212> TYPE: PRT
<213> ORGANISM: Mycobacterium tuberculosis

<400> SEQUENCE: 27

Val Glu Met Ile Glu Ala Val Gly Tyr
1               5

<210> SEQ ID NO 28
<211> LENGTH: 9
<212> TYPE: PRT
<213> ORGANISM: Mycobacterium tuberculosis

<400> SEQUENCE: 28

Val Gly Tyr Arg Ser Trp Pro Arg Tyr
1               5

<210> SEQ ID NO 29
<211> LENGTH: 9
<212> TYPE: PRT
```

<213> ORGANISM: Mycobacterium tuberculosis

<400> SEQUENCE: 29

Arg His Thr Gln Thr Trp Ile Gln Lys
1               5

<210> SEQ ID NO 30
<211> LENGTH: 9
<212> TYPE: PRT
<213> ORGANISM: Mycobacterium tuberculosis

<400> SEQUENCE: 30

His Thr Gln Thr Trp Ile Gln Lys Tyr
1               5

<210> SEQ ID NO 31
<211> LENGTH: 9
<212> TYPE: PRT
<213> ORGANISM: Mycobacterium tuberculosis

<400> SEQUENCE: 31

Asp Ala Ala Ser Leu Arg Pro His Tyr
1               5

<210> SEQ ID NO 32
<211> LENGTH: 9
<212> TYPE: PRT
<213> ORGANISM: Mycobacterium tuberculosis

<400> SEQUENCE: 32

Val Phe Ala Arg Met Trp Glu Leu Tyr
1               5

<210> SEQ ID NO 33
<211> LENGTH: 9
<212> TYPE: PRT
<213> ORGANISM: Mycobacterium tuberculosis

<400> SEQUENCE: 33

Arg Met Trp Glu Leu Tyr Leu Ala Tyr
1               5

<210> SEQ ID NO 34
<211> LENGTH: 9
<212> TYPE: PRT
<213> ORGANISM: Mycobacterium tuberculosis

<400> SEQUENCE: 34

Ser Glu Ala Gly Phe Arg Ser Gly Tyr
1               5

<210> SEQ ID NO 35
<211> LENGTH: 9
<212> TYPE: PRT
<213> ORGANISM: Mycobacterium tuberculosis

<400> SEQUENCE: 35

Phe Arg Ser Gly Tyr Leu Asp Val Tyr
1               5

<210> SEQ ID NO 36
<211> LENGTH: 9
<212> TYPE: PRT
<213> ORGANISM: Mycobacterium tuberculosis -continued

```
<400> SEQUENCE: 36

Ala Arg Ser Leu Asp Pro Ser Arg Tyr
1               5

<210> SEQ ID NO 37
<211> LENGTH: 9
<212> TYPE: PRT
<213> ORGANISM: Mycobacterium tuberculosis

<400> SEQUENCE: 37

Phe Ala Cys Asp Pro Arg Phe Asn Lys
1               5

<210> SEQ ID NO 38
<211> LENGTH: 9
<212> TYPE: PRT
<213> ORGANISM: Mycobacterium tuberculosis

<400> SEQUENCE: 38

Val Pro Ser Glu Glu Val Leu Leu Lys
1               5

<210> SEQ ID NO 39
<211> LENGTH: 9
<212> TYPE: PRT
<213> ORGANISM: Mycobacterium tuberculosis

<400> SEQUENCE: 39

Lys Ile Ala Gln Gly Arg Leu Phe Tyr
1               5

<210> SEQ ID NO 40
<211> LENGTH: 9
<212> TYPE: PRT
<213> ORGANISM: Mycobacterium tuberculosis

<400> SEQUENCE: 40

Phe Tyr Asn Thr Arg Thr Leu Arg Lys
1               5

<210> SEQ ID NO 41
<211> LENGTH: 9
<212> TYPE: PRT
<213> ORGANISM: Mycobacterium tuberculosis

<400> SEQUENCE: 41

Tyr Asn Thr Arg Thr Leu Arg Lys Tyr
1               5

<210> SEQ ID NO 42
<211> LENGTH: 9
<212> TYPE: PRT
<213> ORGANISM: Mycobacterium tuberculosis

<400> SEQUENCE: 42

Arg Lys Tyr Ile Ala Ala Asp Arg Lys
1               5

<210> SEQ ID NO 43
<211> LENGTH: 9
<212> TYPE: PRT
<213> ORGANISM: Mycobacterium tuberculosis

<400> SEQUENCE: 43
```

Ser Ala Arg Leu Ala Gly Ile Pro Tyr
1               5

<210> SEQ ID NO 44
<211> LENGTH: 9
<212> TYPE: PRT
<213> ORGANISM: Mycobacterium tuberculosis

<400> SEQUENCE: 44

Pro Tyr Ile Ala Ile Ala Asn Ala Tyr
1               5

<210> SEQ ID NO 45
<211> LENGTH: 9
<212> TYPE: PRT
<213> ORGANISM: Mycobacterium tuberculosis

<400> SEQUENCE: 45

Pro Val Ser Ile Leu Tyr Arg Leu Tyr
1               5

<210> SEQ ID NO 46
<211> LENGTH: 9
<212> TYPE: PRT
<213> ORGANISM: Mycobacterium tuberculosis

<400> SEQUENCE: 46

Tyr Arg Pro Leu Ile Phe Ala Leu Tyr
1               5

<210> SEQ ID NO 47
<211> LENGTH: 9
<212> TYPE: PRT
<213> ORGANISM: Mycobacterium tuberculosis

<400> SEQUENCE: 47

Leu Pro Leu Asn Trp Leu Arg Arg Lys
1               5

<210> SEQ ID NO 48
<211> LENGTH: 9
<212> TYPE: PRT
<213> ORGANISM: Mycobacterium tuberculosis

<400> SEQUENCE: 48

Cys Arg Ile Phe Thr Asp Gly Asp Tyr
1               5

<210> SEQ ID NO 49
<211> LENGTH: 9
<212> TYPE: PRT
<213> ORGANISM: Mycobacterium tuberculosis

<400> SEQUENCE: 49

Phe Thr Asp Gly Asp Tyr Thr Leu Tyr
1               5

<210> SEQ ID NO 50
<211> LENGTH: 9
<212> TYPE: PRT
<213> ORGANISM: Mycobacterium tuberculosis

<400> SEQUENCE: 50

Asp Val Pro Glu Leu Val Pro Thr Tyr
1               5

```
<210> SEQ ID NO 51
<211> LENGTH: 9
<212> TYPE: PRT
<213> ORGANISM: Mycobacterium tuberculosis

<400> SEQUENCE: 51

Tyr Asn Leu Pro Ala Asn His Arg Tyr
1               5

<210> SEQ ID NO 52
<211> LENGTH: 9
<212> TYPE: PRT
<213> ORGANISM: Mycobacterium tuberculosis

<400> SEQUENCE: 52

Pro Val Leu Trp Ser Pro Asp Val Lys
1               5

<210> SEQ ID NO 53
<211> LENGTH: 9
<212> TYPE: PRT
<213> ORGANISM: Mycobacterium tuberculosis

<400> SEQUENCE: 53

Leu Pro Thr Asp Arg Pro Ile Ile Tyr
1               5

<210> SEQ ID NO 54
<211> LENGTH: 9
<212> TYPE: PRT
<213> ORGANISM: Mycobacterium tuberculosis

<400> SEQUENCE: 54

Ala Thr Leu Gly Ser Ser Gly Gly Lys
1               5

<210> SEQ ID NO 55
<211> LENGTH: 9
<212> TYPE: PRT
<213> ORGANISM: Mycobacterium tuberculosis

<400> SEQUENCE: 55

Ala Thr Ala Gly Arg Asn His Leu Lys
1               5

<210> SEQ ID NO 56
<211> LENGTH: 9
<212> TYPE: PRT
<213> ORGANISM: Mycobacterium tuberculosis

<400> SEQUENCE: 56

Pro Ala Asn Ala Phe Val Ala Asp Tyr
1               5

<210> SEQ ID NO 57
<211> LENGTH: 9
<212> TYPE: PRT
<213> ORGANISM: Mycobacterium tuberculosis

<400> SEQUENCE: 57

Thr Glu Gly Val Ala Ala Ala Val Lys
1               5
```

```
<210> SEQ ID NO 58
<211> LENGTH: 9
<212> TYPE: PRT
<213> ORGANISM: Mycobacterium tuberculosis

<400> SEQUENCE: 58

Ala Gly Leu Thr Ala Ala Asn Thr Lys
1               5

<210> SEQ ID NO 59
<211> LENGTH: 9
<212> TYPE: PRT
<213> ORGANISM: Mycobacterium tuberculosis

<400> SEQUENCE: 59

Gly Leu Thr Ala Ala Asn Thr Lys Lys
1               5

<210> SEQ ID NO 60
<211> LENGTH: 9
<212> TYPE: PRT
<213> ORGANISM: Mycobacterium tuberculosis

<400> SEQUENCE: 60

His Arg Asp Thr Asp Gln Gly Val Tyr
1               5

<210> SEQ ID NO 61
<211> LENGTH: 9
<212> TYPE: PRT
<213> ORGANISM: Mycobacterium tuberculosis

<400> SEQUENCE: 61

Phe Leu Gly Ala Asp Asp Ser Leu Tyr
1               5

<210> SEQ ID NO 62
<211> LENGTH: 9
<212> TYPE: PRT
<213> ORGANISM: Mycobacterium tuberculosis

<400> SEQUENCE: 62

Glu His Glu Pro Ser Asp Leu Val Tyr
1               5

<210> SEQ ID NO 63
<211> LENGTH: 9
<212> TYPE: PRT
<213> ORGANISM: Mycobacterium tuberculosis

<400> SEQUENCE: 63

Phe Asp Leu Asp Arg Leu Leu Phe Lys
1               5

<210> SEQ ID NO 64
<211> LENGTH: 9
<212> TYPE: PRT
<213> ORGANISM: Mycobacterium tuberculosis

<400> SEQUENCE: 64

Asn Ile Cys His Gln Ala Ile Phe Tyr
1               5

<210> SEQ ID NO 65
<211> LENGTH: 9
```

```
<212> TYPE: PRT
<213> ORGANISM: Mycobacterium tuberculosis

<400> SEQUENCE: 65

Gly Leu Phe Gly Thr Ile Gly Pro Tyr
1               5

<210> SEQ ID NO 66
<211> LENGTH: 9
<212> TYPE: PRT
<213> ORGANISM: Mycobacterium tuberculosis

<400> SEQUENCE: 66

Thr Ile Gly Pro Tyr Asn Leu Arg Tyr
1               5

<210> SEQ ID NO 67
<211> LENGTH: 9
<212> TYPE: PRT
<213> ORGANISM: Mycobacterium tuberculosis

<400> SEQUENCE: 67

Ser Asn Pro Ala Leu Val Thr Arg Tyr
1               5

<210> SEQ ID NO 68
<211> LENGTH: 9
<212> TYPE: PRT
<213> ORGANISM: Mycobacterium tuberculosis

<400> SEQUENCE: 68

Tyr Met His Val Val Ala Ser Tyr
1               5

<210> SEQ ID NO 69
<211> LENGTH: 9
<212> TYPE: PRT
<213> ORGANISM: Mycobacterium tuberculosis

<400> SEQUENCE: 69

Gly Leu Ser Asn Thr Ile Val Asp Lys
1               5

<210> SEQ ID NO 70
<211> LENGTH: 9
<212> TYPE: PRT
<213> ORGANISM: Mycobacterium tuberculosis

<400> SEQUENCE: 70

Thr Ile Val Asp Lys Glu Phe Leu Lys
1               5

<210> SEQ ID NO 71
<211> LENGTH: 9
<212> TYPE: PRT
<213> ORGANISM: Mycobacterium tuberculosis

<400> SEQUENCE: 71

Ile Val Leu Val Arg Arg Trp Pro Lys
1               5

<210> SEQ ID NO 72
<211> LENGTH: 9
<212> TYPE: PRT
<213> ORGANISM: Mycobacterium tuberculosis
```

<400> SEQUENCE: 72

Val Ala Arg Arg Gln Arg Ile Leu Phe
1               5

<210> SEQ ID NO 73
<211> LENGTH: 9
<212> TYPE: PRT
<213> ORGANISM: Mycobacterium tuberculosis

<400> SEQUENCE: 73

Thr Leu Ala His Val Val Arg Pro Phe
1               5

<210> SEQ ID NO 74
<211> LENGTH: 9
<212> TYPE: PRT
<213> ORGANISM: Mycobacterium tuberculosis

<400> SEQUENCE: 74

Asp Pro Ser Arg Tyr Glu Val His Phe
1               5

<210> SEQ ID NO 75
<211> LENGTH: 9
<212> TYPE: PRT
<213> ORGANISM: Mycobacterium tuberculosis

<400> SEQUENCE: 75

Val His Phe Ala Cys Asp Pro Arg Phe
1               5

<210> SEQ ID NO 76
<211> LENGTH: 9
<212> TYPE: PRT
<213> ORGANISM: Mycobacterium tuberculosis

<400> SEQUENCE: 76

Asn Lys Leu Leu Gly Pro Leu Pro Phe
1               5

<210> SEQ ID NO 77
<211> LENGTH: 9
<212> TYPE: PRT
<213> ORGANISM: Mycobacterium tuberculosis

<400> SEQUENCE: 77

Leu Lys Ile Ala Gln Gly Arg Leu Phe
1               5

<210> SEQ ID NO 78
<211> LENGTH: 9
<212> TYPE: PRT
<213> ORGANISM: Mycobacterium tuberculosis

<400> SEQUENCE: 78

Trp Ser Pro Gln Ala Arg Arg Arg Phe
1               5

<210> SEQ ID NO 79
<211> LENGTH: 9
<212> TYPE: PRT
<213> ORGANISM: Mycobacterium tuberculosis

<400> SEQUENCE: 79

```
Leu Pro Asp Val Pro Trp Thr Arg Phe
1               5

<210> SEQ ID NO 80
<211> LENGTH: 9
<212> TYPE: PRT
<213> ORGANISM: Mycobacterium tuberculosis

<400> SEQUENCE: 80

Pro Asp Val Pro Trp Thr Arg Phe Phe
1               5

<210> SEQ ID NO 81
<211> LENGTH: 9
<212> TYPE: PRT
<213> ORGANISM: Mycobacterium tuberculosis

<400> SEQUENCE: 81

Gly Val Arg Pro Val Ser Ile Leu Tyr
1               5

<210> SEQ ID NO 82
<211> LENGTH: 9
<212> TYPE: PRT
<213> ORGANISM: Mycobacterium tuberculosis

<400> SEQUENCE: 82

Tyr Arg Leu Tyr Arg Pro Leu Ile Phe
1               5

<210> SEQ ID NO 83
<211> LENGTH: 9
<212> TYPE: PRT
<213> ORGANISM: Mycobacterium tuberculosis

<400> SEQUENCE: 83

Leu Gly Trp Asp Leu Cys Arg Ile Phe
1               5

<210> SEQ ID NO 84
<211> LENGTH: 9
<212> TYPE: PRT
<213> ORGANISM: Mycobacterium tuberculosis

<400> SEQUENCE: 84

Leu Lys Asn Val Pro Ala Asn Ala Phe
1               5

<210> SEQ ID NO 85
<211> LENGTH: 9
<212> TYPE: PRT
<213> ORGANISM: Mycobacterium tuberculosis

<400> SEQUENCE: 85

Lys Gln Val Leu Ser Gly Ala Glu Phe
1               5

<210> SEQ ID NO 86
<211> LENGTH: 9
<212> TYPE: PRT
<213> ORGANISM: Mycobacterium tuberculosis

<400> SEQUENCE: 86

Ala Ala Arg Arg Leu Ala Glu Ala Phe
```

```
1               5
```

<210> SEQ ID NO 87
<211> LENGTH: 9
<212> TYPE: PRT
<213> ORGANISM: Mycobacterium tuberculosis

<400> SEQUENCE: 87

```
Leu Ala Glu Ala Phe Gly Pro Asp Phe
1               5
```

<210> SEQ ID NO 88
<211> LENGTH: 9
<212> TYPE: PRT
<213> ORGANISM: Mycobacterium tuberculosis

<400> SEQUENCE: 88

```
Ala Phe Gly Pro Asp Phe Ala Gly Phe
1               5
```

<210> SEQ ID NO 89
<211> LENGTH: 9
<212> TYPE: PRT
<213> ORGANISM: Mycobacterium tuberculosis

<400> SEQUENCE: 89

```
Lys Val Ala Met Ala Ala Pro Met Phe
1               5
```

<210> SEQ ID NO 90
<211> LENGTH: 9
<212> TYPE: PRT
<213> ORGANISM: Mycobacterium tuberculosis

<400> SEQUENCE: 90

```
Ile Ala Arg Gln Thr Cys Gly Asp Phe
1               5
```

<210> SEQ ID NO 91
<211> LENGTH: 9
<212> TYPE: PRT
<213> ORGANISM: Mycobacterium tuberculosis

<400> SEQUENCE: 91

```
Glu Thr Leu Asp Ile Ala Asn Ile Phe
1               5
```

<210> SEQ ID NO 92
<211> LENGTH: 9
<212> TYPE: PRT
<213> ORGANISM: Mycobacterium tuberculosis

<400> SEQUENCE: 92

```
Leu Ala Thr Gly Thr Trp Leu Leu Phe
1               5
```

<210> SEQ ID NO 93
<211> LENGTH: 9
<212> TYPE: PRT
<213> ORGANISM: Mycobacterium tuberculosis

<400> SEQUENCE: 93

```
Asp Thr Leu Ala Arg Val Ala Ala Phe
1               5
```

<210> SEQ ID NO 94
<211> LENGTH: 9
<212> TYPE: PRT
<213> ORGANISM: Mycobacterium tuberculosis

<400> SEQUENCE: 94

Asp Val Ile Met Arg Ser Thr Asn Phe
1               5

<210> SEQ ID NO 95
<211> LENGTH: 9
<212> TYPE: PRT
<213> ORGANISM: Mycobacterium tuberculosis

<400> SEQUENCE: 95

Thr Asn Phe Arg Trp Gly Gly Ala Phe
1               5

<210> SEQ ID NO 96
<211> LENGTH: 9
<212> TYPE: PRT
<213> ORGANISM: Mycobacterium tuberculosis

<400> SEQUENCE: 96

Ala Phe Asp Leu Asp Arg Leu Leu Phe
1               5

<210> SEQ ID NO 97
<211> LENGTH: 9
<212> TYPE: PRT
<213> ORGANISM: Mycobacterium tuberculosis

<400> SEQUENCE: 97

Arg Asn Ile Cys His Gln Ala Ile Phe
1               5

<210> SEQ ID NO 98
<211> LENGTH: 9
<212> TYPE: PRT
<213> ORGANISM: Mycobacterium tuberculosis

<400> SEQUENCE: 98

Ala Ile Phe Tyr Arg Arg Gly Leu Phe
1               5

<210> SEQ ID NO 99
<211> LENGTH: 9
<212> TYPE: PRT
<213> ORGANISM: Mycobacterium tuberculosis

<400> SEQUENCE: 99

Tyr Arg Val Leu Ala Asp Trp Asp Phe
1               5

<210> SEQ ID NO 100
<211> LENGTH: 9
<212> TYPE: PRT
<213> ORGANISM: Mycobacterium tuberculosis

<400> SEQUENCE: 100

Asp Trp Asp Phe Asn Ile Arg Cys Phe
1               5

<210> SEQ ID NO 101

```
<211> LENGTH: 9
<212> TYPE: PRT
<213> ORGANISM: Mycobacterium tuberculosis

<400> SEQUENCE: 101

Val Val Val Ala Ser Tyr Asn Glu Phe
1               5

<210> SEQ ID NO 102
<211> LENGTH: 9
<212> TYPE: PRT
<213> ORGANISM: Mycobacterium tuberculosis

<400> SEQUENCE: 102

Ser Asn Thr Ile Val Asp Lys Glu Phe
1               5

<210> SEQ ID NO 103
<211> LENGTH: 9
<212> TYPE: PRT
<213> ORGANISM: Mycobacterium tuberculosis

<400> SEQUENCE: 103

Ser Ala Ala Ile Asp Ser Asp Arg Trp
1               5

<210> SEQ ID NO 104
<211> LENGTH: 9
<212> TYPE: PRT
<213> ORGANISM: Mycobacterium tuberculosis

<400> SEQUENCE: 104

Ala Asp Pro Arg Ala Pro Ser Leu Phe
1               5

<210> SEQ ID NO 105
<211> LENGTH: 9
<212> TYPE: PRT
<213> ORGANISM: Mycobacterium tuberculosis

<400> SEQUENCE: 105

Ile Gly Arg His Gly Leu Ile Gly Phe
1               5

<210> SEQ ID NO 106
<211> LENGTH: 9
<212> TYPE: PRT
<213> ORGANISM: Mycobacterium tuberculosis

<400> SEQUENCE: 106

Trp Leu Arg Pro Ile Thr Pro Thr Phe
1               5

<210> SEQ ID NO 107
<211> LENGTH: 9
<212> TYPE: PRT
<213> ORGANISM: Mycobacterium tuberculosis

<400> SEQUENCE: 107

His Tyr Asp Leu Ser Asn Asp Leu Phe
1               5

<210> SEQ ID NO 108
<211> LENGTH: 9
<212> TYPE: PRT
```

<213> ORGANISM: Mycobacterium tuberculosis

<400> SEQUENCE: 108

Leu Ser Asn Asp Leu Phe Ala Ala Phe
1               5

<210> SEQ ID NO 109
<211> LENGTH: 9
<212> TYPE: PRT
<213> ORGANISM: Mycobacterium tuberculosis

<400> SEQUENCE: 109

Thr Met Thr Tyr Ser Cys Ala Met Phe
1               5

<210> SEQ ID NO 110
<211> LENGTH: 9
<212> TYPE: PRT
<213> ORGANISM: Mycobacterium tuberculosis

<400> SEQUENCE: 110

Arg Gln Arg Val Ala Ala Ala Gly Phe
1               5

<210> SEQ ID NO 111
<211> LENGTH: 9
<212> TYPE: PRT
<213> ORGANISM: Mycobacterium tuberculosis

<400> SEQUENCE: 111

Gly Tyr Arg Ser Trp Pro Arg Tyr Phe
1               5

<210> SEQ ID NO 112
<211> LENGTH: 9
<212> TYPE: PRT
<213> ORGANISM: Mycobacterium tuberculosis

<400> SEQUENCE: 112

Leu Ala Thr Arg His Thr Gln Thr Trp
1               5

<210> SEQ ID NO 113
<211> LENGTH: 9
<212> TYPE: PRT
<213> ORGANISM: Mycobacterium tuberculosis

<400> SEQUENCE: 113

Gln Thr Trp Ile Gln Lys Tyr Ile Phe
1               5

<210> SEQ ID NO 114
<211> LENGTH: 9
<212> TYPE: PRT
<213> ORGANISM: Mycobacterium tuberculosis

<400> SEQUENCE: 114

Thr Leu Arg Leu Trp Arg Glu Arg Phe
1               5

<210> SEQ ID NO 115
<211> LENGTH: 9
<212> TYPE: PRT
<213> ORGANISM: Mycobacterium tuberculosis

```
<400> SEQUENCE: 115

Arg Asp Gly Leu Ala His Leu Gly Phe
1               5

<210> SEQ ID NO 116
<211> LENGTH: 9
<212> TYPE: PRT
<213> ORGANISM: Mycobacterium tuberculosis

<400> SEQUENCE: 116

Ala His Leu Gly Phe Asp Glu Val Phe
1               5

<210> SEQ ID NO 117
<211> LENGTH: 9
<212> TYPE: PRT
<213> ORGANISM: Mycobacterium tuberculosis

<400> SEQUENCE: 117

Tyr Leu Ala Tyr Ser Glu Ala Gly Phe
1               5

<210> SEQ ID NO 118
<211> LENGTH: 9
<212> TYPE: PRT
<213> ORGANISM: Mycobacterium tuberculosis

<400> SEQUENCE: 118

Ser Gly Tyr Leu Asp Val Tyr Gln Trp
1               5
```

VACCINES FOR PREVENTION AND TREATMENT OF TUBERCULOSIS

FIELD OF THE INVENTION

The present invention relates to new immunological compositions and vaccines comprising selected *M. tuberculosis* antigens and antigenic peptides as well as nucleic acids encoding said antigens for use in the prevention, prophylaxis and treatment of tuberculosis. In particular the invention provides recombinant BCG based vaccines in which one or more *M. tuberculosis* antigens are overexpressed.

BACKGROUND OF THE INVENTION

Tuberculosis (TB) is one of the major global health issue, and a serious health concern in in many countries, especially in countries where the prevalence and spread of multidrug-resistant tuberculosis (MDR-TB) and extensively drug resistant TB (XDR-TB) has increased during the last few years. Early diagnosis of the disease and the rapid identification of resistance to primary anti-TB drugs are essential for efficient treatment, prevention and control of TB.

The diagnosis of tuberculosis in many countries still relies on tuberculin skin test (TST) and direct sputum examination by light microscopy. TST has low specificity due to cross-reactivity to protein purified derivative (PPD) antigens shared by environmental mycobacteria species, and may give false positive responses in *Bacillus* Calmette-Guerin (BCG) vaccinated individuals, particularly those who received multiple BCG vaccinations. BCG policies vary considerably between countries, primarily depending on the current epidemiological situation.

Interferon-γ release assays (IGRA) have been designed to overcome the problem of cross-reactive T cell immune responses by measuring immune responses to antigens specific for *M. tuberculosis*. Neither the TST nor the IGRA however is able to discriminate between active TB-disease, latent TB infection and previous TB-infection. Exposure to Mycobacteria other than tuberculosis may lead to false-positive results, and poor specificity of the tests may lead to unnecessary prophylactic treatment with anti-tuberculosis drugs. Thus, the ideal diagnostic test should not only discriminate latent TB infection from active TB, but also discriminate between TB, exposure to other Mycobacteria and previous BCG vaccination.

Although latent TB is clinically silent and not contagious, it can reactivate to cause contagious pulmonary TB (Flynn and Chan, *Tuberculosis: latency and reactivation*. Infect Immun, 2001. 69(7): p. 4195-201). Tubercle bacilli are generally considered to be non-replicating in latent TB, yet it may slowly grow and replicate (Munoz-Elias et al., *Replication dynamics of Mycobacterium tuberculosis in chronically infected mice*. Infect Immun, 2005. 73(1): p. 546-51). Latent TB is characterized by highly reduced metabolism and a significantly altered gene expression (Voskuil et al., *Inhibition of respiration by nitric oxide induces a Mycobacterium tuberculosis dormancy program*. J Exp Med, 2003. 198(5): p. 705-13) associated with the different stages of infection (Lin, M. Y. and T. H. Ottenhoff, *Not to wake a sleeping giant: new insights into host-pathogen interactions identify new targets for vaccination against latent Mycobacterium tuberculosis infection*. Biol Chem, 2008. 389(5): p. 497-511). Since most cases of active TB arise in people with latent TB, there is an urgent need to identify new potential targets for TB diagnosis and for development of new and better TB vaccines. Different vaccine targets may be useful for countries with high versus countries with low *M. tuberculosis* burden; or for individuals who have not yet been exposed versus exposed individuals. Thus, a possible solution is the provision of different *M. tuberculosis* vaccines developed, depending on natural *M. tuberculosis* exposures of the target population.

One of the strategies in developing new diagnostic methods and in improving the TB vaccine involves the identification of epitopes in antigens that induce T cell responses. In, addition a strategic choice of the vaccine candidate may be as important, i.e. to choose i) *M. tuberculosis* antigens which are rather not secreted (these may rather serve as 'decoy antigens which prevents the immune system to focus on the biologically and clinically relevant targets), ii) antigens that play a role in *M. tuberculosis* pathogenicity and iii) antigens that are expressed at different points of the *M. tuberculosis* infection and the *M. tuberculosis* life cycle. The antigens according to the present invention fulfill these criteria.

$CD4^+$ T cells play a central role in *M. tuberculosis*—directed cellular immune responses (Endsley et al. *Mycobacterium bovis* BCG vaccination induces memory CD4 T cells characterized by effector biomarker expression and antimycobacterial activity. Vaccine 2007. 25:8384-8394.). It is most likely that an effective tuberculosis (TB) vaccine would target the expansion of $CD8^+$ and $CD4^+$ T cells, which recognize *M. tuberculosis* peptides presented by major histocompatibility complex (MHC) class I and class II molecules. The MHC locus is the most variable gene locus in the human genome, and the variability of MHC class II alleles in different populations is well documented Certain MHC class II alleles have been shown to be associated with *M. tuberculosis* infection (Kettaneh et al. *Human leukocyte antigens and susceptibility to tuberculosis: a metaanalysis of case-control studies*. Int. J. Tuberc. Lung Dis. 2006. 10:717-725). DRB1*0803 and DQB1*0601 were found to be associated with TB disease progression, development of drug resistance, and disease severity in Koreans (Kim et al. *Association of HLA-DR and HLA-DQ genes with susceptibility to pulmonary tuberculosis in Koreans: preliminary evidence of associations with drug resistance, disease severity, and disease recurrence*. Hum. Immunol. 2005. 66:1074-1081). In South Africa, DRB1*1302 and DQB1*0301 to −0304 were apparently associated with active TB compared to control individuals lacking these alleles (Lombard et al. *Association of HLA-DR, -DQ, and vitamin D receptor alleles and haplotypes with tuberculosis in the Venda of South Africa*. Hum. Immunol. 2006. 67:643-654). The prevalence of HLA DRB1* 0401 and HLA-DRB1*0801 was significantly decreased in Mexican patients with pulmonary TB compared to their prevalence in healthy controls (Teran-Escandon et al. *Human leukocyte antigen-associated susceptibility to pulmonary tuberculosis: molecular analysis of class II alleles by DNA amplification and oligonucleotide hybridization in Mexican patients*. Chest 1999. 115:428-433). The association of some MHC class II alleles with "better disease outcome" could be due to the fact that these alleles are "better" at binding and presenting a certain repertoire of peptide epitopes to $CD4^+$ T cells than other alleles Not mutually exclusive, the quality (i.e. differential cytokine production, cytotoxic responses, of a cellular immune response) and the quantity of a cellular response is also biologically and clinically relevant. In addition, it will be of great value where *M. tuberculosis* antigen-specific T-cells reside, i.e. in terminally different effector T-cells (they may produce potent anti-*M. tuberculosis* directed activities, yet they may be short-lived), in memory immune cells or in precursor T-cells which will be able to replenish the T-cell pool once immune memory T-cells and terminally differentiated effector T-cells are not available anymore, e.g. they have succumbed to activation-induced cell death after repetitive antigen-exposure. The preferential expansion of anti-*M. tuberculosis* directed immune responses in different immune T-cell subsets, particularly in precursor T-cells, will therefore be advantageous.

It is not only important where *M. tuberculosis* specific T-cells reside (precursor, immune memory of terminally differentiated T-cells), yet also the nature of the target antigens. The identification of peptides binding to molecularly defined MHC class II alleles could therefore represent an important first step in identifying potential targets for TB vaccine design and the development of new diagnostic assays. More recently, De Groot and colleagues used a bioinformatics approach, followed by validation with functional assays to identify $CD4^+$ T-cell epitopes that were used to construct an epitope-based *M. tuberculosis* vaccine (*Developing an epitope-driven tuberculosis (TB) vaccine*. Vaccine 2005. 23:2121-2131). Only a few *M. tuberculosis* MHC class II binding peptides have been identified so far, and 7% of the *M. tuberculosis* open reading frames have been explored for both B-cell and T-cell epitopes (Blythe et al. *An analysis of the epitope knowledge related to mycobacteria*. Immunome Res. 2007. 3:10). Peptide microarray assay has the major advantage that a high number of candidate peptides can be screened within a short time frame. Gaseitsiwe et al. (*Peptide microarray-based identification of Mycobacterium tuberculosis epitope binding to HLA-DRB*1*0101, *DRB*1*1501 *and DRB*1*0401. Clin Vacc Immunol 2010, 17:168-175) describe *M. tuberculosis* peptide binding to the three most frequently encountered MHC class II alleles in different populations; DRB1*0101, DRB1*1501, and DRB1*0401. DRB1*0101, DRB1*1501, and DRB1*0401 exhibit population frequencies of 15.4%, 32.9%, and 20.9% among Caucasians. In the Botswana population, HLA-DRB1*01, -DRB1*02, and -DRB1*04 show population frequencies of 21.7%, 21.3%, and 14.4%, respectively. 7,446 unique peptides derived from 61 *M. tuberculosis* proteins were tested. In addition, *M. tuberculosis* targets can be recognized by serum antibodies. This is not only relevant concerning immunoglobulin-mediated recognition, it is also an indirect measurement of T-cell activation and recognition, since strong IgG-responses require strong CD4+ T-cell help (Gaseitsiwe et al. supra; Gaseitsiwe et al. Pattern recognition in pulmonary tuberculosis defined by high content peptide microarray chip analysis representing 61 proteins from *M. tuberculosis*. PLoS ONE. 2008; 3(12):e3840. Epub 2008 Dec. 9).

SUMMARY OF THE INVENTION

The present inventors have identified three antigens from *Mycobacterium tuberculosis,* a) Putative cyclopropane-fatty-acyl-phospholipid synthase (GenBank Accession No. CAA17404) encoded by locus Rv0447c as shown in SEQ ID NO:1,
b) Possible glycosyltransferase (GenBank Accession No. CAB05418) encoded by locus Rv2958c as shown in SEQ ID NO:2, and
c) Possible glycosyltransferase (GenBank Accession No. CAB05419) encoded by locus Rv2957 as shown in SEQ ID NO:3 as being specifically important for the immunological response to i) infections by *M. tuberculosis* ii) infection with mycobacterial species and iii) vaccination targeting *M. tuberculosis* and/or other mycobacterial species.

Accordingly, in one aspect the present invention provides vaccines and immunological compositions comprising one or more polypeptides selected from i) the polypeptide SEQ ID NO:1,
ii) a polypeptide being a functional variant of the polypeptide i) which has an amino acid sequence which is more than 50%, more than 75%, such as more than 80%, more than 90%, or even more preferably more than 95% identical to the sequence SEQ ID NO:1,
iii) the polypeptide SEQ ID NO:2,
iv) a polypeptide being a functional variant of the polypeptide iii) which has an amino acid sequence which is more than 50%, more than 75%, such as more than 80%, more than 90%, or even more preferably more than 95% identical to the sequence SEQ ID NO:2,
v) the polypeptide SEQ ID NO:3,
vi) a polypeptide being a functional variant of the polypeptide v) which has an amino acid sequence which is more than 50%, more than 75%, such as more than 80%, more than 90%, or even more preferably more than 95% identical to the sequence SEQ ID NO:3, and
vii) a polypeptide comprising one or more functional fragment of any one of the polypeptides (i)-(vi), said fragment comprising an immunogenic portion, e.g. a T-cell epitope, of said polypeptide.

Preferably the vaccine or immunological composition comprises two or more polypeptides selected from the polypeptides (i)-(vii), such as three or more, such as 4, 5, 6, 7, 8, 9, 10 or more polypeptides selected from the polypeptides (i)-(vii).

The polypeptide vii) can comprise 2 or more functional fragments, such as 3, 4, 5, 6, 7, 8, 9, 10 or more functional fragments of any one of the polypeptides (i)-(vi).

The functional fragment(s) of any one of the polypeptides (i)-(vi) can comprise a peptide sequence selected from the sequences SEQ ID NO: 4-118.

The functional fragment(s) preferably comprise(s) a peptide sequence selected from the sequences SEQ ID NO: 4-17.

The functional fragment(s) can consist of a peptide sequence selected from the sequences SEQ ID NO: 4-17.

In another aspect the present invention provides vaccines and immunological compositions comprising one or more nucleic acid sequences selected from nucleic acids encoding one or more polypeptides selected from i) the polypeptide SEQ ID NO:1,
ii) a polypeptide being a functional variant of the polypeptide i) which has an amino acid sequence which is more than 50%, more than 75%, such as more than 80%, more than 90%, or even more preferably more than 95% identical to the sequence SEQ ID NO:1,
iii) the polypeptide SEQ ID NO:2,
iv) a polypeptide being a functional variant of the polypeptide iii) which has an amino acid sequence which is more than 50%, more than 75%, such as more than 80%, more than 90%, or even more preferably more than 95% identical to the sequence SEQ ID NO:2,
v) the polypeptide SEQ ID NO:3,
vi) a polypeptide being a functional variant of the polypeptide v) which has an amino acid sequence which is more than 50%, more than 75%, such as more than 80%, more than 90%, or even more preferably more than 95% identical to the sequence SEQ ID NO:3, and
vii) a polypeptide comprising one or more functional fragment of any one of the polypeptides (i)-(vi), said fragment comprising an immunogenic portion, e.g. a T-cell epitope of said polypeptide.

Preferably the vaccine or immunological composition comprises two or more nucleic acid sequences selected from nucleic acids encoding polypeptides selected from the polypeptides (i)-(vii), such as three or more, such as 4, 5, 6, 7, 8, 9, 10 or more nucleic acid sequences encoding polypeptides selected from the polypeptides (i)-(vii).

The polypeptide vii) can comprise two or more functional fragments, such as 3, 4, 5, 6, 7, 8, 9, 10 or more functional fragments of any one of the polypeptides (i)-(vi).

The functional fragment(s) of any one of the polypeptides (i)-(vi) can comprise a peptide sequence selected from the sequences SEQ ID NO: 4-118.

The functional fragment preferably comprises a peptide sequence selected from the sequences SEQ ID NO: 4-17.

The functional fragment can consist of a peptide sequence selected from the sequences SEQ ID NO: 4-17.

The nucleic acid can be a deoxyribonucleic acid (DNA) or ribonucleic acid (RNA). Said nucleic acid can be delivered by a viral, bacterial, or plant cell vector. Preferably the viral vector is an adenoviral vector. Preferably the bacterial vector is mycobacterial vector.

In another aspect the present invention provides recombinant Bacille Calmette-Guerin (BCG) comprising one or more nucleic acid sequence selected from nucleic acids encoding one or more polypeptides selected from
  i) the polypeptide SEQ ID NO:1,
  ii) a polypeptide being a functional variant of the polypeptide i) which has an amino acid sequence which is more than 50%, more than 75%, such as more than 80%, more than 90%, or even more preferably more than 95% identical to the sequence SEQ ID NO:1,
  iii) the polypeptide SEQ ID NO:2,
  iv) a polypeptide being a functional variant of the polypeptide iii) which has an amino acid sequence which is more than 50%, more than 75%, such as more than 80%, more than 90%, or even more preferably more than 95% identical to the sequence SEQ ID NO:2,
  v) the polypeptide SEQ ID NO:3,
  vi) a polypeptide being a functional variant of the polypeptide v) which has an amino acid sequence which is more than 50%, more than 75%, such as more than 80%, more than 90%, or even more preferably more than 95% identical to the sequence SEQ ID NO:3, and
  vii) a polypeptide comprising one or more functional fragment of any one of the polypeptides (i)-(vi), said fragment comprising an immunogenic portion, e.g. a T-cell epitope, of said polypeptide.
wherein said nucleic acid sequences are overexpressed.

Preferably the vaccine or immunological composition comprises two or more nucleic acid sequences selected from nucleic acids encoding polypeptides selected from the polypeptides (i)-(vii), such as three or more, such as 4, 5, 6, 7, 8, 9, 10 or more nucleic acid sequences encoding polypeptides selected from the polypeptides (i)-(vii).

The polypeptide vii) can comprise two or more functional fragments, such as 3, 4, 5, 6, 7, 8, 9, 10 or more functional fragments of any one of the polypeptides (i)-(vi).

The functional fragment(s) of any one of the polypeptides (i)-(vi) can comprise a peptide sequence selected from the sequences SEQ ID NO: 1-118.

The functional fragment preferably comprises a peptide sequence selected from the sequences SEQ ID NO: 4-17.

The functional fragment can consist of a peptide sequence selected from the sequences SEQ ID NO: 4-17.

The recombinant BCG can further comprise a nucleic acid encoding a perfringolysin wherein said nucleic acid sequence is expressed by the BCG.

In another aspect the present invention provides an immunological composition comprising a recombinant BCG according to the invention.

In another aspect the present invention provides a vaccine composition comprising a recombinant BCG according to the invention.

The present inventors have further identified peptides derived from the three *M. tuberculosis* antigens
  a) Putative cyclopropane-fatty-acyl-phospholipid synthase (GenBank Accession No. CAA17404) as shown in SEQ ID NO:1,
  b) Possible glycosyltransferase (GenBank Accession No. CAB05418) as shown in SEQ ID NO:2, and
  c) Possible glycosyltransferase (GenBank Accession No. CAB05419) as shown in SEQ ID NO:3, peptides which are demonstrated to bind to the common MHC class I alleles HLA-A*0201, HLA-A*2402, HLA-A*3001, HLA-A*3002, HLA-A*6801, HLA-B*5801, and HLA-C*0701.

Accordingly, in one aspect the present invention provides isolated peptides of between 7 and 20 amino acids in length comprising a sequence of at least 7 consecutive amino acids, preferably at least 8 consecutive amino acids, more preferably at least 9 consecutive amino acids derived from the sequence of a polypeptide selected from the polypeptides a) Putative cyclopropane-fatty-acyl-phospholipid synthase (GenBank Accession No. CAA17404) as shown in SEQ ID NO:1,
b) Possible glycosyltransferase (GenBank Accession No. CAB05418) as shown in SEQ ID NO:2, and
c) Possible glycosyltransferase (GenBank Accession No. CAB05419) as shown in SEQ ID NO:3.

The peptides can be of between 7 and 20, such as between 8 and 20, or between 9 and 20 amino acids in length.

Preferably, the peptides according to the invention are selected from the group of peptides consisting of the peptides SEQ ID NOs: 4-118.

More preferably, the peptides according to the invention are selected from the group of peptides consisting of the peptides

SEQ ID NO: 4
VLAGSVDEL,

SEQ ID NO: 5
KYIFPGGLL,

SEQ ID NO: 6
RMWELYLAY,

SEQ ID NO: 7
AASAAIANR,

SEQ ID NO: 8
ALADLPVTV,

SEQ ID NO: 9
KYIAADRKI,

SEQ ID NO: 10
SARLAGIPY,

SEQ ID NO: 11
AAPEPVARR,

SEQ ID NO: 12
ATLGSSGGK,

```
                                SEQ ID NO: 13
        ATAGRNHLK,

SEQ ID NO: 14
        SIIIPTLNV,

SEQ ID NO: 15
        PYNLRYRVL,

SEQ ID NO: 16
        IVLVRRWPK,
        and

SEQ ID NO: 17
        LVYGDVIMR.
```

The peptides SEQ ID NOs. 4-7 being derived from Putative cyclopropane-fatty-acyl-phospholipid synthase (GenBank Accession No. CAA17404) as shown in SEQ ID NO:1, and the peptides SEQ ID NOs: 8-13 being derived from Possible glycosyltransferase (GenBank Accession No. CAB05418) as shown in SEQ ID NO:2, and the peptides SEQ NOs: 14-17 being derived from Possible glycosyltransferase (GenBank Accession No. CAB05419) as shown in SEQ ID NO:3.

In another aspect the present invention provides vaccines and immunological compositions comprising one or more peptides according to the invention.

In another aspect the present invention provides vaccines and immunological compositions comprising one or more nucleic acid sequences selected from nucleic acids encoding one or more peptides according to the invention.

The nucleic acid can be a deoxyribonucleic acid (DNA) or ribonucleic acid (RNA). Said nucleic acid can be delivered by a viral, bacterial, or plant cell vector. Preferably the viral vector is an adenoviral vector. Preferably the bacterial vector is mycobacterial vector.

In one embodiment the vaccines according to the invention can be used for naivê vaccination of a subject not earlier exposed to a mycobacterial infection or vaccination, including *M. tuberculosis* and BCG and/or any other mycobacterial species, exemplified, but not limited to, *M. africanum* and *M. bovis* (*M. tuberculosis* complex), and MOTT (*mycobacterium* other than tuberculosis), i.e. *M. avium intracellulare*, *M. avium*, *M. avium* intracellular complex, *M. ulcerans*, *M. fortuitum*, *M. xenopi*, *M. marinum*, *M. hemophilum*, *M. abscessus*, *M. szulgai*, *M. kansasii*, *M. chelonae*, as well as *M. leprae*.

In another embodiment the vaccines according to the invention is for therapeutic vaccination of a subject already exposed to a mycobacterial infection. The mycobacterial infection to be treated is exemplified, but not limited to, *M. tuberculosis* infection, BCG infection, and infections caused by *M. africanum* and *M. bovis* (*M. tuberculosis* complex), yet also MOTT (*mycobacterium* other than tuberculosis), i.e. *M. avium intracellulare*, *M. avium*, *M. avium* intracellular complex, *M. ulcerans*, *M. fortuitum*, *M. xenopi*, *M. marinum*, *M. hemophilum*, *M. abscessus*, *M. szulgai*, *M. kansasii*, *M. chelonae*, as well as *M. leprae*.

The individual to be vaccinated can be suffering from active *M. tuberculosis* infection, or the individual to be vaccinated can be suffering from latent *M. tuberculosis* infection.

The vaccines and immunological compositions according to the invention can further comprise additional mycobacterial or other antigens, which can be in the form of DNA, RNA, peptides and/or polypeptides.

The vaccines and immunological compositions according to the invention can further comprise an adjuvant and/or one or more pharmaceutical acceptable excipient or carrier.

The vaccines and immunological compositions according to the invention can be formulated for different routes of administration, such as oral administration, nasal administration, intra muscular administration, subcutaneous administration, intracutaneous, intradermal, subdermal or as an antigen preparation exposed to skin or any inner- or outer body surface alone or along with a carrier.

In another aspect the present invention provides methods for immunizing a subject against infection caused by a mycobacterial species or for eliciting an immune response to a mycobacterial species in said subject, comprising the step of administering to said subject a vaccine composition or an immunological composition according to the invention. The mycobacterial species is exemplified, but not limited to, *M. tuberculosis*, BCG, *M. africanum* and *M. bovis* (*M. tuberculosis* complex), yet also MOTT (*mycobacterium* other than tuberculosis), i.e. *M. avium intracellulare*, *M. avium*, *M. avium* intracellular complex, *M. ulcerans*, *M. fortuitum*, *M. xenopi*, *M. marinum*, *M. hemophilum*, *M. abscessus*, *M. szulgai*, *M. kansasii*, *M. chelonae*, as well as *M. leprae*.

In another aspect the present invention provides methods for treating a subject having an infection caused by a mycobacterial species comprising the step of administering to said subject a vaccine composition or an immunological composition according to the invention. The mycobacterial species is exemplified, but not limited to, *M. tuberculosis*, BCG, *M. africanum* and *M. bovis* (*M. tuberculosis* complex), yet also MOTT (*mycobacterium* other than tuberculosis), i.e. *M. avium intracellulare*, *M. avium*, *M. avium* intracellular complex, *M. ulcerans*, *M. fortuitum*, *M. xenopi*, *M. marinum*, *M. hemophilum*, *M. abscessus*, *M. szulgai*, *M. kansasii*, *M. chelonae*, as well as *M. leprae*.

The subject to be treated can be suffering from active *M. tuberculosis* infection, or the subject to be treated can be suffering from latent *M. tuberculosis* infection. Similarly, the subject may also suffer from any other infection associated with a mycobacterial species.

In another aspect the present invention provides methods for prevention and/or prophylaxis of recurrence of symptoms of tuberculosis in a subject with a latent mycobacterial infection, comprising the step of administering to said patient a vaccine composition or an immunological composition according to the invention. The mycobacterial infection is exemplified, but not limited to *M. tuberculosis* infections, BCG infections, and infections caused by *M. africanum* and *M. bovis* (*M. tuberculosis* complex), yet also MOTT (*mycobacterium* other than tuberculosis), i.e. *M. avium intracellulare*, *M. avium*, *M. avium* intracellular complex, *M. ulcerans*, *M. fortuitum*, *M. xenopi*, *M. marinum*, *M. hemophilum*, *M. abscessus*, *M. szulgai*, *M. kansasii*, *M. chelonae*, as well as *M. leprae*.

The subject can be any mammal, such as a cow, the subject is preferably a human.

In another aspect the present invention provides methods for determining the immune response in an individual following vaccination or immunization, the method comprising the use of one or more peptides and/or one or more polypeptides according to the invention.

The method can preferably be an in vitro method.

The peptide to be used can be any peptide of between 7 to 20 amino acids in length comprising a sequence of at least 7 consecutive amino acids, preferably at least 8 consecutive amino acids, more preferably at least 9 consecutive amino acids derived from the sequence of a polypeptide selected from the polypeptides
  a) Putative cyclopropane-fatty-acyl-phospholipid synthase (GenBank Accession No. CAA17404) as shown in SEQ ID NO:1,
  b) Possible glycosyltransferase (GenBank Accession No. CAB05418) as shown in SEQ ID NO:2, and
  c) Possible glycosyltransferase (GenBank Accession No. CAB05419) as shown in SEQ ID NO:3.

The peptides can be of between 7 and 20, such as between 8 and 20, or between 9 and 20 amino acids in length.

Preferably the peptide is a peptide comprising a sequence corresponding to any of SEQ ID NOs 4-118.

More preferably the peptide is a peptide comprising a sequence corresponding to any of SEQ ID NOs 4-17.

The polypeptides to be used can be any polypeptide selected from
  i) the polypeptide SEQ ID NO:1,
  ii) a polypeptide being a functional variant of the polypeptide i) which has an amino acid sequence which is more than 50%, more than 75%, such as more than 80%, more than 90%, or even more preferably more than 95% identical to the sequence SEQ ID NO:1,
  iii) the polypeptide SEQ ID NO:2,
  iv) a polypeptide being a functional variant of the polypeptide iii) which has an amino acid sequence which is more than 50%, more than 75%, such as more than 80%, more than 90%, or even more preferably more than 95% identical to the sequence SEQ ID NO:2,
  v) the polypeptide SEQ ID NO:3,
  vi) a polypeptide being a functional variant of the polypeptide v) which has an amino acid sequence which is more than 50%, more than 75%, such as more than 80%, more than 90%, or even more preferably more than 95% identical to the sequence SEQ ID NO:3, and
  vii) a polypeptide comprising one or more functional fragment of any one of the polypeptides (i)-(vi), said fragment comprising an immunogenic portion, e.g. a T-cell epitope of said polypeptide.

The method can comprise the determination of T-cell binding and/or reactivity to one or more of said peptides and/or one or more of said polypeptides.

T-cell reactivity can be measured in different ways. Objective enumeration of antigen-specific T-cells can be carried out using soluble MHC Class I or—class I molecules loaded with the nominal target peptides. The MHC/peptide complex is usually coupled to a fluorescent dye and the MHC/peptide complexes are presented as multimers to enable interaction with the T-cell receptor. Enumeration of antigen-specific T-cells can be carried out using flow cytometry in combination with T-cell markers. The addition of T-cell activation markers, e.g. CD38, CD25, CD69, HLA-DR will also help to differentiate between non-stimulated and stimulated T-cells.

Alternate ways to detect T-cell function are: specific intracellular events associated with recognition of the nominal target structure, e.g. reflected by phosphorylation of cellular proteins. T-cell effector functions are also used to gauge T-cell reactivity, e.g. production of cytokines, cytotoxicity either measured by killing of target cells, or detection of alterations associated with cytotoxicity, i.e. membrane trafficking, CD107a expression and perforin, granzyme detection. A biologically important T-cell function is also T-cell proliferation.

Cytokine production can be measured in several ways, e.g. in determining cytokine production in cell culture supernants after exposure to the nominal target protein, partial protein stretches or peptides. The detection of intracellular cytokine production requires the use of peptides since this assay is usually performed within a 6 hour time frame—which does not allow take up, process and present complex antigens. Therefore, peptides, presenting the nominal target are being used in this assay. They are able to bind to different MHC class I and—class II molecules—and, in some cases, also to non-classical MHC molecules and to CD1 antigens. The assay requires that the entire protein sequence is used as the peptide sources since we have no detailed information concerning the genetic background of the patients and which peptide species is exactly presented from a particular MHC class I or—class II molecules to antigen-specific T-cells. This is hard to predict since some peptide binding motifs are still ill-defined. Upon recognition, cytokines are produced and can be visualized using specific monoclonal antibodies by flow cytometry.

In another aspect the present invention provides methods for diagnosing, characterizing, or classifying a mycobacterial infection the method comprising the use of one or more peptides and/or one or more polypeptides according to the invention.

The method can preferably be an in vitro method.

The peptide to be used can be any peptide of between 7 to 20 amino acids in length comprising a sequence of at least 7 consecutive amino acids, preferably at least 8 consecutive amino acids, more preferably at least 9 consecutive amino acids derived from the sequence of a polypeptide selected from the polypeptides
  a) Putative cyclopropane-fatty-acyl-phospholipid synthase (GenBank Accession No. CAA17404) as shown in SEQ ID NO:1,
  b) Possible glycosyltransferase (GenBank Accession No. CAB05418) as shown in SEQ ID NO:2, and
  c) Possible glycosyltransferase (GenBank Accession No. CAB05419) as shown in SEQ ID NO:3.

The peptides can be of between 7 and 20, such as between 8 and 20, or between 9 and 20 amino acids in length.

Preferably the peptide is a peptide comprising a sequence corresponding to any of SEQ ID NOs 4-118.

More preferably the peptide is a peptide comprising a sequence corresponding to any of SEQ ID NOs 4-17.

The polypeptides to be used can be any polypeptide selected from
  i) the polypeptide SEQ ID NO:1,
  ii) a polypeptide being a functional variant of the polypeptide i) which has an amino acid sequence which is more than 50%, more than 75%, such as more than 80%, more than 90%, or even more preferably more than 95% identical to the sequence SEQ ID NO:1,
  iii) the polypeptide SEQ ID NO:2,
  iv) a polypeptide being a functional variant of the polypeptide iii) which has an amino acid sequence which is more than 50%, more than 75%, such as more than 80%, more than 90%, or even more preferably more than 95% identical to the sequence SEQ ID NO:2,
  v) the polypeptide SEQ ID NO:3,
  vi) a polypeptide being a functional variant of the polypeptide v) which has an amino acid sequence which is more than 50%, more than 75%, such as more than 80%, more than 90%, or even more preferably more than 95% identical to the sequence SEQ ID NO:3, and
  vii) a polypeptide comprising one or more functional fragment of any one of the polypeptides (i)-(vi), said fragment comprising an immunogenic portion, e.g. a T-cell epitope of said polypeptide.

The mycobacterial infection is exemplified by, but not limited to, *M. tuberculosis* infection, BCG infection, and infections caused by *M. africanum* and *M. bovis* (*M. tuberculosis* complex), yet also MOTT (*mycobacterium* other than tuberculosis), i.e. *M. avium intracellulare*, *M. avium*, *M. avium* intracellular complex, *M. ulcerans*, *M. fortuitum*, *M. xenopi*, *M. marinum*, *M. hemophilum*, *M. abscessus*, *M. szulgai*, *M. kansasii*, *M. chelonae*, as well as *M. leprae*.

In another aspect the present invention provides methods for diagnosing, characterizing, or classifying exposure to *M. tuberculosis*, vaccination with BCG, vaccination with the said protein or exposure to any other mycobacterial species. The method comprising the use of one or more peptides and/or one or more polypeptides according to the invention.

The method can preferably be an in vitro method.

The peptide to be used can be any peptide of between 7 to 20 amino acids in length comprising a sequence of at least 7 consecutive amino acids, preferably at least 8 consecutive amino acids, more preferably at least 9 consecutive amino acids derived from the sequence of a polypeptide selected from the polypeptides a) Putative cyclopropane-fatty-acyl-phospholipid synthase (GenBank Accession No. CAA17404) as shown in SEQ ID NO:1,
b) Possible glycosyltransferase (GenBank Accession No. CAB05418) as shown in SEQ ID NO:2, and
c) Possible glycosyltransferase (GenBank Accession No. CAB05419) as shown in SEQ ID NO:3.

The peptides can be of between 7 and 20, such as between 8 and 20, or between 9 and 20 amino acids in length.

Preferably the peptide is a peptide comprising a sequence corresponding to any of SEQ ID NOs 4-118.

More preferably the peptide is a peptide comprising a sequence corresponding to any of SEQ ID NOs 4-17.

The polypeptides to be used can be any polypeptide selected from
i) the polypeptide SEQ ID NO:1,
ii) a polypeptide being a functional variant of the polypeptide i) which has an amino acid sequence which is more than 50%, more than 75%, such as more than 80%, more than 90%, or even more preferably more than 95% identical to the sequence SEQ ID NO:1,
iii) the polypeptide SEQ ID NO:2,
iv) a polypeptide being a functional variant of the polypeptide iii) which has an amino acid sequence which is more than 50%, more than 75%, such as more than 80%, more than 90%, or even more preferably more than 95% identical to the sequence SEQ ID NO:2,
v) the polypeptide SEQ ID NO:3,
vi) a polypeptide being a functional variant of the polypeptide v) which has an amino acid sequence which is more than 50%, more than 75%, such as more than 80%, more than 90%, or even more preferably more than 95% identical to the sequence SEQ ID NO:3, and
vii) a polypeptide comprising one or more immunogenic portion, e.g. a T-cell epitope, of any one of the polypeptides (i)-(vi).

The method can comprise the determination of T-cell binding and/or reactivity to one or more of said peptides and/or one or more of said polypeptides.

It is contemplated that any method or composition described herein can be implemented with respect to any other method or composition described herein. Similarly, any embodiment discussed with respect to one aspect of the invention may be used in the context of any other aspect of the invention.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 12 shows the effect of MAP kinase inhibitors on COX-2 and SOCS-3 protein expression in human monocyte cell line (THP1) stimulated with the CAB05419/Rv2957; CAB05418/Rv2958c and CAA17404/Rv0477c antigens.

DETAILED DESCRIPTION OF THE INVENTION

Figure 1:
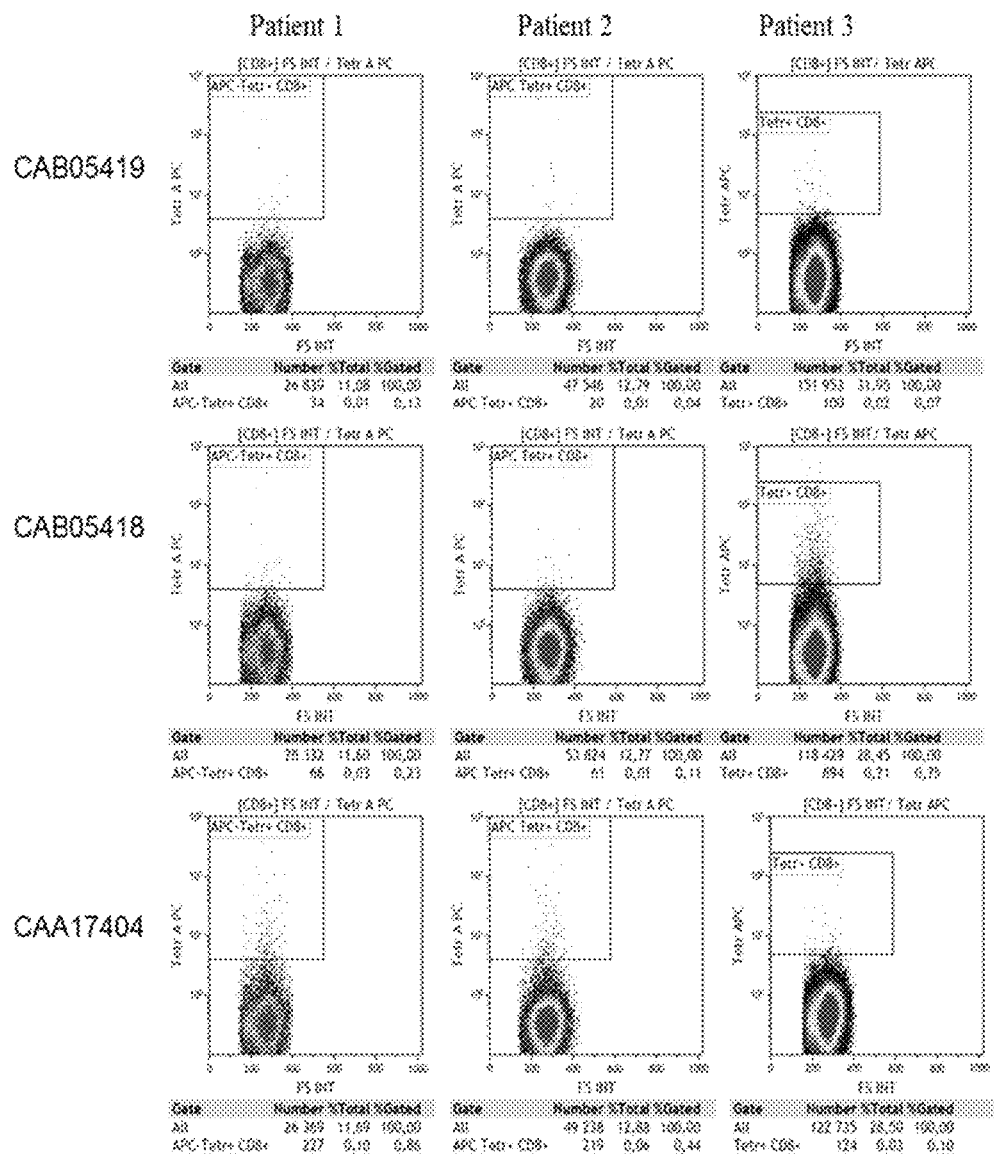
FIG. 1 shows detection of MHC class I *M. tuberculosis* antigen specific recognition by CD3+CD8+ T-cells measured by flow cytometry.

Specifically, the peptides listed in Table 1 are good binders to the most frequent MHC class I alleles in Caucasians and individuals with Asian descent. Listed are peptides binding to HLA-A*0201, HLA-A*2402 and HLA-A*6801.

TABLE 1

MHC class 1 binding to HLA-A*0201, HLA-A*2402 and HLA-A*6801

|  | CAA17404 |  | CAB05418 |  | CAB05419 |  |
|---|---|---|---|---|---|---|
| Seq | Seq | SEQ ID NO score | Seq | SEQ ID NO score | Seq | SEQ ID NO score |
| A*0201 | VLAGSVDEL | 4   31 | ALADLPVTV | 8   30 | SIIIPTLNV | 14   26 |
| A*2402 | KYIFPGGLL | 5   25 | KYIAADRKI | 9   25 | PYNLRYRVL | 15   21 |
| A*6801 | AASAAIANR | 7   24 | AAPEPVARR | 11   24 | LVYGDVIMR | 17   26 |

The peptides were derived from the proteins Putative cyclopropane-fatty-acyl-phospholipid synthase (GenBank Accession No. CAA17404) SEQ ID NO:1, Possible glycosyltransferase (GenBank Accession No. CAB05418) SEQ ID NO:2, and Possible glycosyltransferase (GenBank Accession No. CAB05419) SEQ ID NO:3, respectively.

Peptides derived from these proteins were also used to identify peptides binding to the most frequent African alleles, i.e. HLA-A*3001 and HLA-A*3002. The peptides tested are listed in Table 2.

TABLE 2

Candidate peptides for testing on HLA-A3001/3002.

| Peptide ID | Sequence | Protein | SEQ ID NO |
|---|---|---|---|
| 1 | SDRWPAVAK | CAA17404 | 18 |
| 2 | THLPLRLVY | CAA17404 | 19 |
| 3 | GLIGFGESY | CAA17404 | 20 |
| 4 | YMAGEWSSK | CAA17404 | 21 |
| 5 | ARRNIAVHY | CAA17404 | 22 |
| 6 | AFLDETMTY | CAA17404 | 23 |
| 7 | ELAAAQRRK | CAA17404 | 24 |
| 8 | RVEIDLCDY | CAA17404 | 25 |
| 9 | DYRDVDGQY | CAA17404 | 26 |
| 10 | VEMIEAVGY | CAA17404 | 27 |

TABLE 2 -continued

Candidate peptides for testing on HLA-A3001/3002.

| Peptide ID | Sequence | Protein | SEQ ID NO |
|---|---|---|---|
| 11 | VGYRSWPRY | CAA17404 | 28 |
| 12 | RHTQTWIQK | CAA17404 | 29 |
| 13 | HTQTWIQKY | CAA17404 | 30 |
| 14 | DAASLRPHY | CAA17404 | 31 |
| 15 | VFARMWELY | CAA17404 | 32 |
| 16 | RMWELYLAY | CAA17404 | 33 |
| 17 | SEAGFRSGY | CAA17404 | 34 |
| 18 | FRSGYLDVY | CAA17404 | 35 |
| 19 | ARSLDPSRY | CAB05418 | 36 |
| 20 | FACDPRFNK | CAB05418 | 37 |
| 21 | VPSEEVLLK | CAB05418 | 38 |
| 22 | KIAQGRLFY | CAB05418 | 39 |
| 23 | FYNTRTLRK | CAB05418 | 40 |
| 24 | YNTRTLRKY | CAB05418 | 41 |
| 25 | RKYIAADRK | CAB05418 | 42 |
| 26 | SARLAGIPY | CAB05418 | 43 |
| 27 | PYIAIANAY | CAB05418 | 44 |
| 29 | PVSILYRLY | CAB05418 | 45 |
| 30 | YRPLIFALY | CAB05418 | 46 |
| 31 | LPLNWLRRK | CAB05418 | 47 |
| 32 | CRIFTDGDY | CAB05418 | 48 |
| 33 | FTDGDYTLY | CAB05418 | 49 |
| 34 | DVPELVPTY | CAB05418 | 50 |
| 35 | YNLPANHRY | CAB05418 | 51 |
| 36 | PVLWSPDVK | CAB05418 | 52 |
| 37 | LPTDRPIIY | CAB05418 | 53 |
| 38 | ATLGSSGGK | CAB05418 | 54 |
| 39 | ATAGRNHLK | CAB05418 | 55 |
| 40 | PANAFVADY | CAB05418 | 56 |
| 41 | TEGVAAAVK | CAB05418 | 57 |
| 42 | AGLTAANTK | CAB05419 | 58 |
| 43 | GLTAANTKK | CAB05419 | 59 |
| 44 | HRDTDQGVY | CAB05419 | 60 |
| 45 | FLGADDSLY | CAB05419 | 61 |
| 46 | EHEPSDLVY | CAB05419 | 62 |
| 47 | FDLDRLLFK | CAB05419 | 63 |
| 48 | NICHQAIFY | CAB05419 | 64 |

TABLE 2 -continued

Candidate peptides for testing on HLA-A3001/3002.

| Peptide ID | Sequence | Protein | SEQ ID NO |
|---|---|---|---|
| 49 | GLFGTIGPY | CAB05419 | 65 |
| 50 | TIGPYNLRY | CAB05419 | 66 |
| 51 | SNPALVTRY | CAB05419 | 67 |
| 52 | YMHVVVASY | CAB05419 | 68 |
| 53 | GLSNTIVDK | CAB05419 | 69 |
| 54 | TIVDKEFLK | CAB05419 | 70 |
| 55 | IVLVRRWPK | CAB05419 | 71 |

We have also identified MHC class I binding peptides from the antigens binding to the most frequent African alleles, i.e. HLA-A*3001 and HLA-A*3002 displayed in Table 2.

HLA-A*3002 binds much more MHC class I peptides as compared to HLA-A*3001, which is very selective in the choice of peptide ligands. Table 3 and Table 4 below.

TABLE 3

Peptides binding to HLA-A*3002.

| Peptide ID | Sequence | Binding % |
|---|---|---|
| 1 | SDRWPAVAK | 0 |
| 2 | THLPLRLVY | 46.7 |
| 3 | GLIGFGESY | 30.1 |
| 4 | YMAGEWSSK | 87.5 |
| 5 | ARRNIAVHY | 74.5 |
| 6 | AFLDETMTY | 63.2 |
| 7 | ELAAAQRRK | 53.3 |
| 8 | RVEIDLCDY | 98.5 |
| 9 | DYRDVDGQY | 36.2 |
| 10 | VEMIEAVGY | 58.5 |
| 11 | VGYRSWPRY | 94.1 |
| 12 | RHTQTWIQK | 81.8 |
| 13 | HTQTWIQKY | 90.8 |
| 14 | DAASLRPHY | 28.5 |
| 15 | VFARMWELY | 94.8 |
| 16 | RMWELYLAY | 98.3 |
| 17 | SEAGFRSGY | 80 |
| 18 | FRSGYLDVY | 102.9 |
| 19 | ARSLDPSRY | 97.8 |
| 20 | FACDPRFNK | 81.8 |
| 21 | VPSEEVLLK | 86.9 |
| 22 | KIAQGRLFY | 164.5 |
| 23 | FYNTRTLRK | 77.2 |
| 24 | YNTRTLRKY | 112.1 |
| 25 | RKYIAADRK | 88.7 |
| 26 | SARLAGIPY | 118.2 |
| 27 | PYIAIANAY | 83.5 |
| 28 | GVRPVSILY | 20.8 |
| 29 | PVSILYRLY | 113.7 |
| 30 | YRPLIFALY | 75.3 |
| 31 | LPLNWLRRK | 75.7 |
| 32 | CRIFTDGDY | 111.9 |
| 33 | FTDGDYTLY | 38.2 |
| 34 | DVPELVPTY | 23.7 |
| 35 | YNLPANHRY | 104.1 |
| 36 | PVLWSPDVK | 45.5 |
| 37 | LPTDRPIIY | 64.6 |
| 38 | ATLGSSGGK | 109.8 |
| 39 | ATAGRNHLK | 91 |
| 40 | PANAFVADY | 115.2 |
| 41 | TEGVAAAVK | 19 |
| 42 | AGLTAANTK | 35.7 |
| 43 | GLTAANTKK | 58.3 |
| 44 | HRDTDQGVY | 90.6 |
| 45 | FLGADDSLY | 113.8 |
| 46 | EHEPSDLVY | 97.2 |
| 47 | FDLDRLLFK | 39.1 |
| 48 | NICHQAIFY | 49.6 |
| 49 | GLFGTIGPY | 79.1 |
| 50 | TIGPYNLRY | 113 |
| 51 | SNPALVTRY | 57.1 |
| 52 | YMHVVVASY | 98.5 |
| 53 | GLSNTIVDK | 124.1 |
| 54 | TIVDKEFLK | 107 |
| 55 | IVLVRRWPK | 114.2 |

Table 3 shows that HLA-A*3002 binds a high number of candidate epitopes.

TABLE 4

Selective binding of HLA-A*3001 to candidate target peptides.

| Peptide ID | Sequence | Binding % |
|---|---|---|
| 1 | SDRWPAVAK | 0 |
| 2 | THLPLRLVY | 0 |
| 3 | GLIGFGESY | 0 |
| 4 | YMAGEWSSK | 0 |
| 5 | ARRNIAVHY | 0 |
| 6 | AFLDETMTY | 0 |
| 7 | ELAAAQRRK | 1.3 |
| 8 | RVEIDLCDY | 7.7 |
| 9 | DYRDVDGQY | 4.2 |
| 10 | VEMIEAVGY | 0 |
| 11 | VGYRSWPRY | 4.4 |
| 12 | RHTQTWIQK | 5.5 |
| 13 | HTQTWIQKY | 0 |
| 14 | DAASLRPHY | 0 |
| 15 | VFARMWELY | 9.4 |
| 16 | RMWELYLAY | 15.9 |
| 17 | SEAGFRSGY | 12.1 |
| 18 | FRSGYLDVY | 9 |
| 19 | ARSLDPSRY | 22.1 |
| 20 | FACDPRFNK | 23.3 |
| 21 | VPSEEVLLK | 0 |
| 22 | KIAQGRLFY | 12.2 |
| 23 | FYNTRTLRK | 29.3 |
| 24 | YNTRTLRKY | 6.3 |
| 25 | RKYIAADRK | 8.7 |
| 26 | SARLAGIPY | 69.8 |
| 27 | PYIAIANAY | 5.8 |
| 28 | GVRPVSILY | 12 |
| 29 | PVSILYRLY | 6.1 |
| 30 | YRPLIFALY | 15.6 |
| 31 | LPLNWLRRK | 27.5 |
| 32 | CRIFTDGDY | 32.2 |
| 33 | FTDGDYTLY | 25.1 |
| 34 | DVPELVPTY | 22.7 |
| 35 | YNLPANHRY | 29.9 |
| 36 | PVLWSPDVK | 26.4 |
| 37 | LPTDRPIIY | 10.1 |
| 38 | ATLGSSGGK | 51.5 |
| 39 | ATAGRNHLK | 137.9 |
| 40 | PANAFVADY | 30.3 |
| 41 | TEGVAAAVK | 29 |
| 42 | AGLTAANTK | 28.5 |
| 43 | GLTAANTKK | 21.4 |
| 44 | HRDTDQGVY | 27.3 |
| 45 | FLGADDSLY | 13.8 |
| 46 | EHEPSDLVY | 13.5 |
| 47 | FDLDRLLFK | 10.3 |
| 48 | NICHQAIFY | 7.9 |
| 49 | GLFGTIGPY | 6.5 |
| 50 | TIGPYNLRY | 6.5 |
| 51 | SNPALVTRY | 5.6 |
| 52 | YMHVVVASY | 1.8 |
| 53 | GLSNTIVDK | 16.2 |
| 54 | TIVDKEFLK | 22.9 |
| 55 | IVLVRRWPK | 151.2 |

Table 4 shows that HLA-A*3001 is much more 'selective' concerning peptide binding than HLA-A*3002 selection, only peptides 26, 38, 39, and 55 show high binding.

Table 5 lists peptides which bind both HLA-A*3001 and HLA-*3002. Note the very high binding of individual peptides which is higher (therefore more than 100%) as compared to the placeholder control peptide.

TABLE 5

MHC class I binding peptides to HLA-A30.

| Peptide ID | Sequence | A*3001 Binding % | A*3002 Binding % |
|---|---|---|---|
| 26 | SARLAGIPY | 69.8 | 118.2 |
| 38 | ATLGSSGGK | 51.5 | 109.8 |
| 39 | ATAGRNHLK | 137.9 | 91 |
| 55 | IVLVRRWPK | 151.2 | 114.2 |

TABLE 6

Peptides binding to HLA-B*5801 and HLA-C*0701

| Protein | Peptide | SEQ ID NO | B*5801 binding | C*0701 binding |
|---|---|---|---|---|
| CAB05418 | VARRQRILF | 72 | + | + |
| CAB05418 | TLAHVVRPF | 73 | | + |
| CAB05418 | DPSRYEVHF | 74 | | + |

TABLE 6 -continued

Peptides binding to HLA-B*5801 and HLA-C*0701

| Protein | Peptide | SEQ ID NO | B*5801 binding | C*0701 binding |
|---|---|---|---|---|
| CAB05418 | VHFACDPRF | 75 | | + |
| CAB05418 | NKLLGPLPF | 76 | | + |
| CAB05418 | LKIAQGRLF | 77 | | + |
| CAB05418 | KIAQGRLFY | 39 | | + |
| CAB05418 | YNTRTLRKY | 41 | | + |
| CAB05418 | SARLAGIPY | 43 | + | + |
| CAB05418 | PYIAIANAY | 44 | | + |
| CAB05418 | WSPQARRRF | 78 | + | + |
| CAB05418 | LPDVPWTRF | 79 | | + |
| CAB05418 | PDVPWTRFF | 80 | | + |
| CAB05418 | GVRPVSILY | 81 | | + |
| CAB05418 | PVSILYRLY | 45 | | + |
| CAB05418 | YRLYRPLIF | 82 | | + |
| CAB05418 | YRPLIFALY | 46 | | + |
| CAB05418 | LGWDLCRIF | 83 | | + |
| CAB05418 | CRIFTDGDY | 48 | | + |
| CAB05418 | FTDGDYTLY | 49 | + | + |
| CAB05418 | DVPELVPTY | 50 | | + |
| CAB05418 | YNLPANHRY | 51 | | + |
| CAB05418 | LPTDRPIIY | 53 | | + |
| CAB05418 | LKNVPANAF | 84 | | + |
| CAB05418 | PANAFVADY | 56 | + | + |
| CAB05418 | KQVLSGAEF | 85 | | + |
| CAB05418 | AARRLAEAF | 86 | + | + |
| CAB05418 | LAEAFGPDF | 87 | + | + |
| CAB05418 | AFGPDFAGF | 88 | | + |
| CAB05419 | HRDTDQGVY | 60 | | + |
| CAB05419 | KVAMAAPMF | 89 | | + |
| CAB05419 | IARQTCGDF | 90 | + | + |
| CAB05419 | ETLDIANIF | 91 | + | + |
| CAB05419 | LATGTWLLF | 92 | + | + |
| CAB05419 | FLGADDSLY | 61 | | + |
| CAB05419 | DTLARVAAF | 93 | + | + |
| CAB05419 | EHEPSDLVY | 62 | | + |
| CAB05419 | DVIMRSTNF | 94 | | + |
| CAB05419 | TNFRWGGAF | 95 | | + |
| CAB05419 | AFDLDRLLF | 96 | | + |
| CAB05419 | RNICHQAIF | 97 | | + |
| CAB05419 | NICHQAIFY | 64 | | + |
| CAB05419 | AIFYRRGLF | 98 | | + |
| CAB05419 | GLFGTIGPY | 65 | | + |
| CAB05419 | TIGPYNLRY | 66 | | + |
| CAB05419 | YRVLADWDF | 99 | | + |
| CAB05419 | DWDFNIRCF | 100 | | + |
| CAB05419 | SNPALVTRY | 67 | | + |
| CAB05419 | YMHVVVASY | 68 | | + |
| CAB05419 | VVVASYNEF | 101 | | + |
| CAB05419 | SNTIVDKEF | 102 | | + |
| CAA17404 | SAAIDSDRW | 103 | + | |
| CAA17404 | THLPLRLVY | 19 | | + |
| CAA17404 | ADPRAPSLF | 104 | | + |
| CAA17404 | IGRHGLIGF | 105 | + | + |
| CAA17404 | GLIGFGESY | 20 | | + |
| CAA17404 | WLRPITPTF | 106 | | + |
| CAA17404 | ARRNIAVHY | 22 | | + |
| CAA17404 | HYDLSNDLF | 107 | | + |
| CAA17404 | LSNDLFAAF | 108 | + | + |
| CAA17404 | AFLDETMTY | 23 | | + |
| CAA17404 | TMTYSCAMF | 109 | | + |
| CAA17404 | RQRVAAAGF | 110 | | + |
| CAA17404 | RVEIDLCDY | 25 | | + |
| CAA17404 | DYRDVDGQY | 26 | | + |
| CAA17404 | VEMIEAVGY | 27 | | + |
| CAA17404 | VGYRSWPRY | 28 | + | + |
| CAA17404 | GYRSWPRYF | 111 | | + |
| CAA17404 | LATRHTQTW | 112 | + | |
| CAA17404 | HTQTWIQKY | 30 | + | + |
| CAA17404 | QTWIQKYIF | 113 | + | + |
| CAA17404 | DAASLRPHY | 31 | + | + |
| CAA17404 | TLRLWRERF | 114 | | + |
| CAA17404 | RDGLAHLGF | 115 | | + |
| CAA17404 | AHLGFDEVF | 116 | | + |
| CAA17404 | VFARMWELY | 32 | | + |
| CAA17404 | RMWELYLAY | 33 | | + |
| CAA17404 | YLAYSEAGF | 117 | | + |

TABLE 6 -continued

Peptides binding to HLA-B*5801 and HLA-C*0701

| Protein | Peptide | SEQ ID NO | B*5801 binding | C*0701 binding |
|---------|---------|-----------|----------------|----------------|
| CAA17404 | SEAGFRSGY | 34 | | + |
| CAA17404 | FRSGYLDVY | 35 | | + |
| CAA17404 | SGYLDVYQW | 118 | + | + |

These data could have not been predicted using in silico methods. They could only be identified using recombinantly expressed MHC class I molecules used to measure objectively peptide binding.

These data demonstrate how peptides derived from the three polypeptides according to the invention can form stable MHC class I molecules—which can be used to target CD8+ T-cell responses, either in a vaccine, or in a diagnostic or prognostic setting.

TABLE 7

List of epitopes

| Protein | Amino acid nos | Peptide | SEQ ID NO |
|---------|----------------|---------|-----------|
| CAB05418 | 27-35 | VARRQRILF | 72 |
| CAB05418 | 41-39 | TLAHVVRPF | 73 |
| CAB05418 | 52-60 | ARSLDPSRY | 36 |
| CAB05418 | 56-64 | DPSRYEVHF | 74 |
| CAB05418 | 62-70 | VHFACDPRF | 75 |
| CAB05418 | 64-72 | FACDPRFNK | 37 |
| CAB05418 | 71-79 | NKLLGPLPF | 76 |
| CAB05418 | 87-95 | VPSEEVLLK | 38 |
| CAB05418 | 94-82 | LKIAQGRLF | 77 |
| CAB05418 | 95-103 | KIAQGRLFY | 39 |
| CAB05418 | 102-110 | FYNTRTLRK | 40 |
| CAB05418 | 103-111 | YNTRTLRKY | 41 |
| CAB05418 | 109-117 | RKYIAADRK | 42 |
| CAB05418 | 138-146 | SARLAGIPY | 43 |
| CAB05418 | 145-153 | PYIAIANAY | 44 |
| CAB05418 | 154-162 | WSPQARRRF | 78 |
| CAB05418 | 164-172 | LPDVPWTRF | 79 |
| CAB05418 | 165-173 | PDVPWTRFF | 80 |
| CAB05418 | 174-182 | GVRPVSILY | 81 |
| CAB05418 | 177-185 | PVSILYRLY | 45 |
| CAB05418 | 182-190 | YRLYRPLIF | 82 |
| CAB05418 | 185-193 | YRPLIFALY | 46 |
| CAB05418 | 195-203 | LPLNWLRRK | 47 |
| CAB05418 | 209-317 | LGWDLCRIF | 83 |
| CAB05418 | 214-222 | CRIFTDGDY | 48 |
| CAB05418 | 217-225 | FTDGDYTLY | 49 |
| CAB05418 | 227-235 | DVPELVPTY | 50 |
| CAB05418 | 235-243 | YNLPANHRY | 51 |
| CAB05418 | 246-254 | PVLWSPDVK | 52 |
| CAB05418 | 262-270 | LPTDRPIIY | 53 |
| CAB05418 | 271-279 | ATLGSSGGK | 54 |
| CAB05418 | 299-307 | ATAGRNHLK | 55 |
| CAB05418 | 306-314 | LKNVPANAF | 84 |
| CAB05418 | 310-318 | PANAFVADY | 56 |
| CAB05418 | 390-398 | KQVLSGAEF | 85 |
| CAB05418 | 401-409 | AARRLAEAF | 85 |
| CAB05418 | 405-413 | LAEAFGPDF | 87 |
| CAB05418 | 408-416 | AFGPDFAGF | 88 |
| CAB05419 | 9-17 | GLTAANTKK | 59 |
| CAB05419 | 84-92 | HRDTDQGVY | 60 |
| CAB05419 | 17-25 | KVAMAAPMF | 89 |
| CAB05419 | 45-53 | IARQTCGDF | 90 |
| CAB05419 | 65-73 | ETLDIANIF | 91 |
| CAB05419 | 101-109 | LATGTWLLF | 92 |
| CAB05419 | 109-117 | FLGADDSLY | 61 |
| CAB05419 | 120-128 | DTLARVAAF | 93 |
| CAB05419 | 131-139 | EHEPSDLVY | 62 |
| CAB05419 | 141-149 | DVIMRSTNF | 94 |
| CAB05419 | 147-155 | TNFRWGGAF | 95 |
| CAB05419 | 154-162 | AFDLDRLLF | 96 |
| CAB05419 | 164-172 | RNICHQAIF | 97 |
| CAB05419 | 165-173 | NICHQAIFY | 64 |
| CAB05419 | 170-178 | AIFYRRGLF | 98 |
| CAB05419 | 176-184 | GLFGTIGPY | 65 |
| CAB05419 | 180-188 | TIGPYNLRY | 66 |
| CAB05419 | 188-196 | YRVLADWDF | 99 |
| CAB05419 | 193-201 | DWDFNIRCF | 100 |
| CAB05419 | 202-210 | SNPALVTRY | 67 |
| CAB05419 | 210-218 | YMHVVVASY | 68 |
| CAB05419 | 213-221 | VVVASYNEF | 101 |
| CAB05419 | 223-231 | GLSNTIVDK | 69 |
| CAB05419 | 225-233 | SNTIVDKEF | 102 |
| CAB05419 | 227-235 | TIVDKEFLK | 70 |

TABLE 7 -continued

List of epitopes

| Protein | Amino acid nos | Peptide | SEQ ID NO |
|---|---|---|---|
| CAB05419 | 249-257 | IVLVRRWPK | 71 |
| CAA17404 | 10-18 | SAAIDSDRW | 103 |
| CAA17404 | 46-54 | THLPLRLVY | 19 |
| CAA17404 | 63-71 | ADPRAPSLF | 104 |
| CAA17404 | 82-90 | IGRHGLIGF | 105 |
| CAA17404 | 86-94 | GLIGFGESY | 20 |
| CAA17404 | 94-102 | YMAGEWSSK | 21 |
| CAA17404 | 125-133 | WLRPITPTF | 106 |
| CAA17404 | 145-153 | ARRNIAVHY | 22 |
| CAA17404 | 152-160 | HYDLSNDLF | 107 |
| CAA17404 | 155-163 | LSNDLFAAF | 108 |
| CAA17404 | 162-170 | AFLDETMTY | 23 |
| CAA17404 | 167-175 | TMTYSCAMF | 109 |
| CAA17404 | 188-196 | ELAAAQRRK | 24 |
| CAA17404 | 247-255 | RQRVAAAGF | 110 |
| CAA17404 | 258-266 | RVEIDLCDY | 25 |
| CAA17404 | 265-273 | DYRDVDGQY | 26 |
| CAA17404 | 279-287 | VEMIEAVGY | 27 |
| CAA17404 | 285-293 | VGYRSWPRY | 28 |
| CAA17404 | 286-294 | GYRSWPRYF | 111 |
| CAA17404 | 320-328 | LATRHTQTW | 112 |
| CAA17404 | 323-331 | RHTQTWIQK | 29 |
| CAA17404 | 324-332 | HTQTWIQKY | 30 |
| CAA17404 | 326-334 | QTWIQKYIF | 113 |
| CAA17404 | 359-367 | DAASLRPHY | 31 |
| CAA17404 | 370-378 | TLRLWRERF | 114 |
| CAA17404 | 382-390 | RDGLAHLGF | 115 |
| CAA17404 | 387-395 | AHLGFDEVF | 116 |
| CAA17404 | 393-401 | VFARMWELY | 32 |
| CAA17404 | 396-404 | RMWELYLAY | 33 |
| CAA17404 | 401-409 | YLAYSEAGF | 117 |
| CAA17404 | 405-413 | SEAGFRSGY | 34 |
| CAA17404 | 409-417 | FRSGYLDVY | 35 |
| CAA17404 | 411-419 | SGYLDVYQW | 118 |

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1. Peptide Binding to HLA-A Alleles

Peptide binding analysis is performed in the following way: First, MHC class I antigens are cloned and expressed as recombinant proteins, along with the non-covalently bound beta-2 microglobulin. The MHC-class I peptide complex is folded with the addition of a place holder peptide which yields a trimolecular complex—associated with changes in the shape of the MHC class I heavy chain—this exposes an epitope which is recognized by a monoclonal antibody. The trimolecular complex (MHC class I heavy chain/beta-2 microglobulin/place holder peptide) is then dissociated and washed. Only the free-floating MHC class I heavy chain remains. Test peptides are added (one test peptide/readout) and excess beta-2 microglobulin). If the candidate peptide binds, then the trimolecular complex is reconstituted and this can be detected using a specific conformation-dependent antibody. Note that MHC class I binding of candidate peptides does not imply necessarily that T-cells are present directed against that complex in vivo in an organism. Therefore, multimer complexes have to be prepared, labeled with a fluorescent dye and implemented to gauge MHC class I peptide complex—specific T-cells from a clinically very well defined population. Such an example is shown in the FIG. 1 below.

Example 2. Tetramer Staining of Patient T-Cells

Tetramer Construction.

MHC class I heavy chain molecules: Bacterial expression vectors (pET24d+ and pHN1), containing the nucleotide sequences for the soluble part of the heavy chain of the MHC class I alleles and the light chain β2m were used to produce the recombinant proteins. The gene for HLA-A*3001 was obtained by altering the HLA-A*3002 sequence by site-directed mutagenesis (kit from Stratagene, La Jolla, USA). The following mutations were made: c282g, a299t, a301g and c526t. Any other MHC class I molecules were cloned from 4-digit typed PBMC samples.

Recombinant Proteins

The recombinant MHC class I molecules (heavy and light chains) were as inclusion bodies in *E. coli* B121 DE3 pLys (Invitrogen, Carlsbad, Calif.) and solubilized in urea buffer (all chemicals: Sigma-Aldrich Sweden AB, Stockholm, Sweden). The heavy and the light chains were folded with an allele-specific peptide (JPT Peptide Technologies GmbH, Berlin) during three days in a tris-arginine buffer. The folded monomers were concentrated and biotinylated using the enzyme BirA (Avidity, Aurora, USA). The biotinylated monomers were concentrated and affinity-purified using an avidin column (Thermo Fisher Scientific, Rockford, USA).

Binding Assay:

Nonamer peptides overlapping by 8aa covering the entire TB10.4 sequence, (total number of 88 peptides), were synthesized by JPT Peptide Technologies GmbH, Berlin, Germany.

Peptide-binding, affinity, and off-rate experiments were performed in duplicates in iTopia 96-well plates coated with different recombinant MHC class I molecules (human leukocyte antigen (HLA). Briefly, monomer-coated plates are stripped of the placeholder peptide leaving the heavy chain free to associate with a candidate peptide after addition of β-2 microglobulin. Peptide binding to MHC class molecules is detected after 18 h incubation at 21° C. with a fluorescent-labeled antibody (anti-HLA A, B, C-FITC), which binds only to the trimeric complex.

Each candidate peptide was tested against an appropriate control peptide, specific for each MHC class I molecule and results are reported in % binding as compared to the control peptide. A more detailed analysis of the binding characteristics of each individual peptide was performed using affinity and off-rate assays.

Off-Rate:

MHC class I-peptide complex stability was analyzed by incubating bound peptides at 37° C. for eight different time points. The off-rate is expressed as a t½ value, which is defined as the time point when 50% of the initial peptide concentration has dissociated from the MHC class I-peptide molecule complex.

Affinity Assay:

MHC class I allele-peptide affinity for individual peptide species was measured using different peptide concentrations ($10^{-4}$ to $10^{-9}$ M) followed by calculating the peptide quantity needed to achieve 50% binding saturation (the ED50 value).

Calculations:

Values of peptide binding, affinity, and off-rate were calculated using the iTopia™ System Software. Sigmoidal dose response curves were generated using Prism® 4.0 (GraphPad).

Cellular Analysis:

Peripheral blood mononuclear cells (PBMCs) from patients with pulmonary tuberculosis were obtained by separation over a Ficoll gradient. Patients were diagnosed for pulmonary TB based on acid-fast staining and bacterial culture; they had given their consent to participate in this study. Ethical approval was documented. The patients were MHC class I typed at the Blood Bank, University of Mainz. Tetramers were prepared for the MHC class I alleles and labeled with strepavidin-phycoerytin (PE) or streptavidin-allophycocyanin (APC). Flow cytometric analysis was performed and positive events, i.e. antigen-specific T-cells, were identified as percent per CD3+CD8+ T-cells. At least 50 000 events were obtained in the CD3+, CD8+, CD4-, CD13- and CD19-negative population. The following antibodies (Abs) obtained from Beckman Coulter were used: anti-CD3-ECD (clone CHT1), anti-CD8α-FITC (clone T8) (positive gating) and anti-CD4-Pcy5 (clone 13B8.2), anti-CD13-Pcy5 (clone SJ1D1) and anti-CD19-Pcy5 (clone J4.119) for negative gating. Positive tetramer staining was compared to staining with the iTag negative control Tetramer. Flow cytometry analysis was performed using an FC500 flow cytometer from Beckman Coulter.

Detection of MHC class I *M. tuberculosis* antigen specific recognition using MHC class I multimers complexed with the nominal target peptides according to the invention are presented in FIG. 1. The allele here is for all three individuals HLA-A*2402.

FIG. 1 describes identification of MHC class I binding epitopes to frequent MHC class I alleles and tetramer-guided ex vivo detection of CD8+ T-cells recognizing epitopes from the above listed *M. tuberculosis* target proteins.

Example 3. Intracellular Cytokine Staining (ICS)

Detection of polyfunctional T-cell producing simultaneously IL-2, IFNγ and TNFα directed to cyclopropane-fatty-acyl-phospholipid synthase CAA17404 in peripheral blood mononuclear cells (PBMCs) from a non-human primate protected from *M. tuberculosis* infection.

Figure 2:
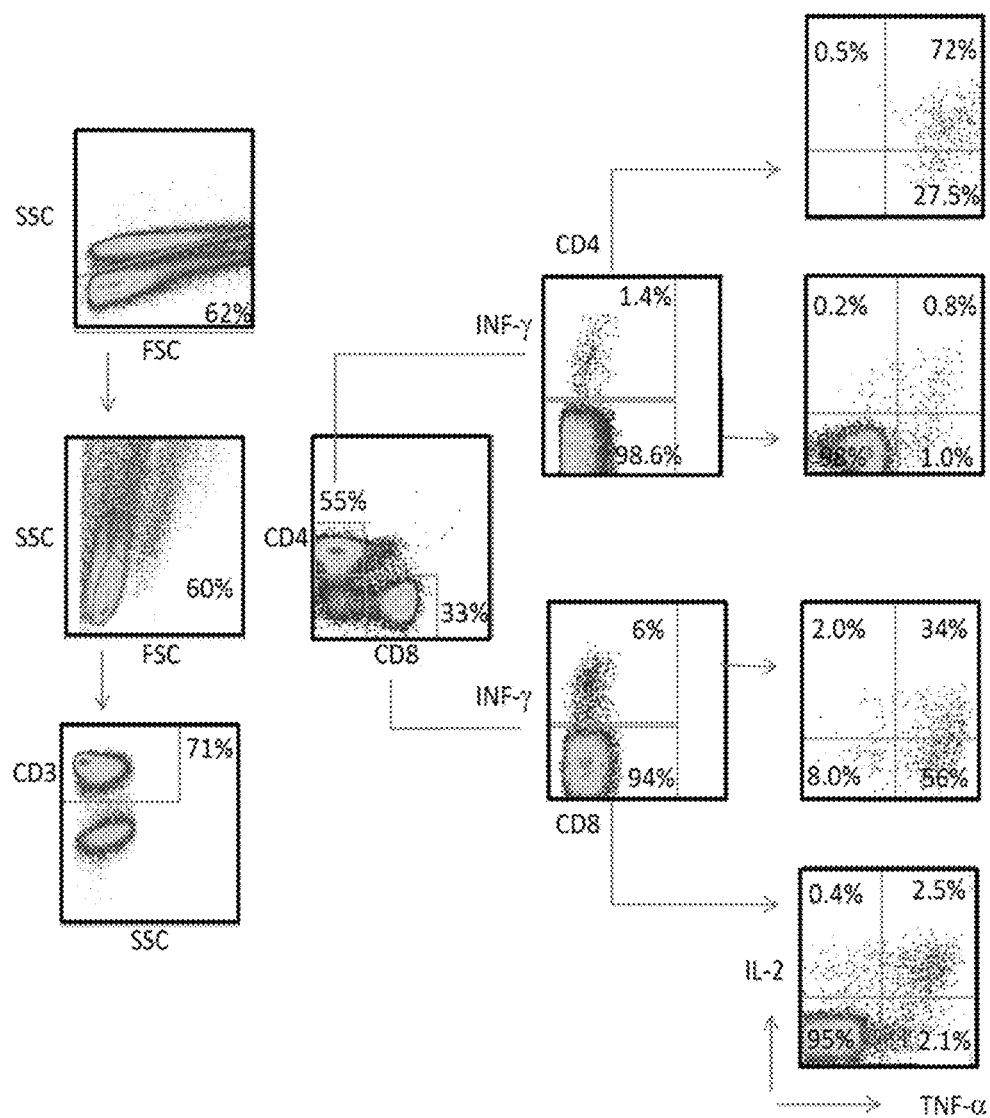
FIG. 2 shows detection of polyfunctional T-cell simultaneously producing IL-2, IFN-γ and TNFα directed to Cyclopropane-fatty-acyl-phospholipid synthase CAA17404.

Results are presented in FIG. 2.

Detection of intracellular cytokines, here represented by IL-2, in response to Possible glycosyltransferases CAB05419/CAB05418 and Cyclopropane-fatty-acyl-phospholipid synthase CAA17404 in PBMCs from a monkey vaccinated with BCG.

Figure 3:
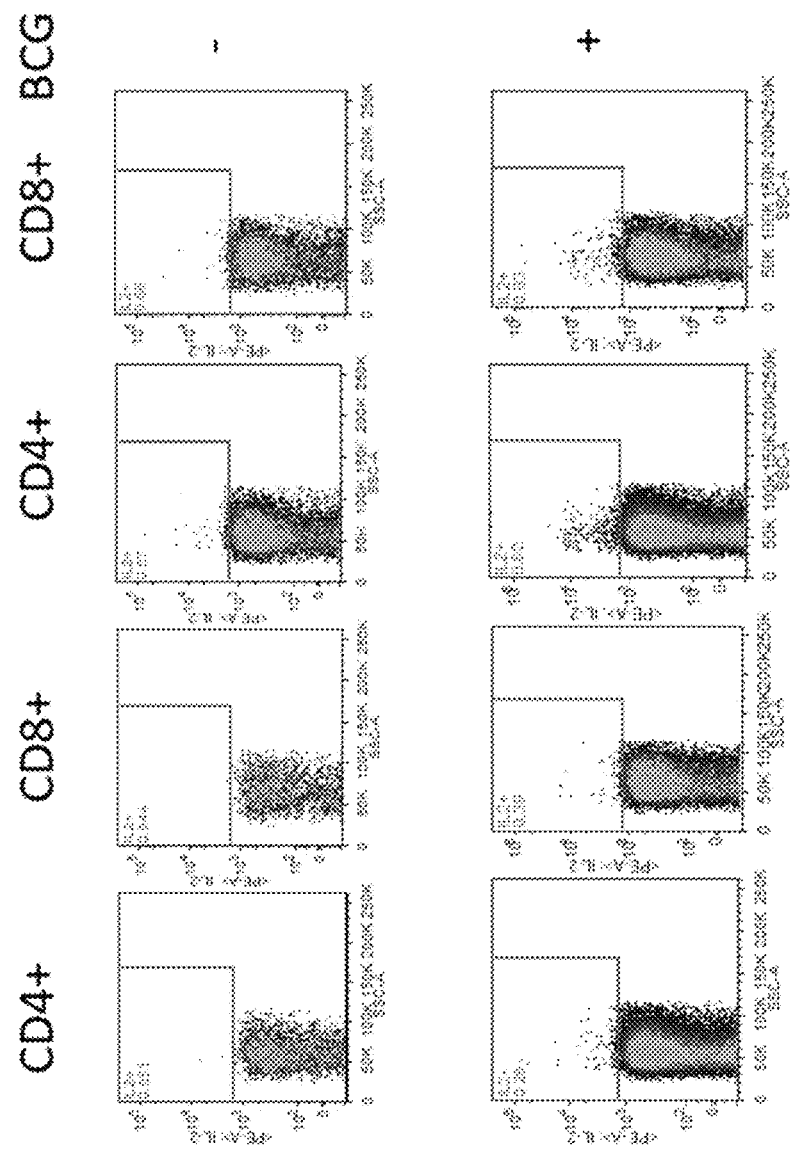
FIG. 3 shows detection of intracellular IL-2, in PBMCs from a monkey vaccinated with BCG.

Results are presented in FIG. 3.

Figure 4A:
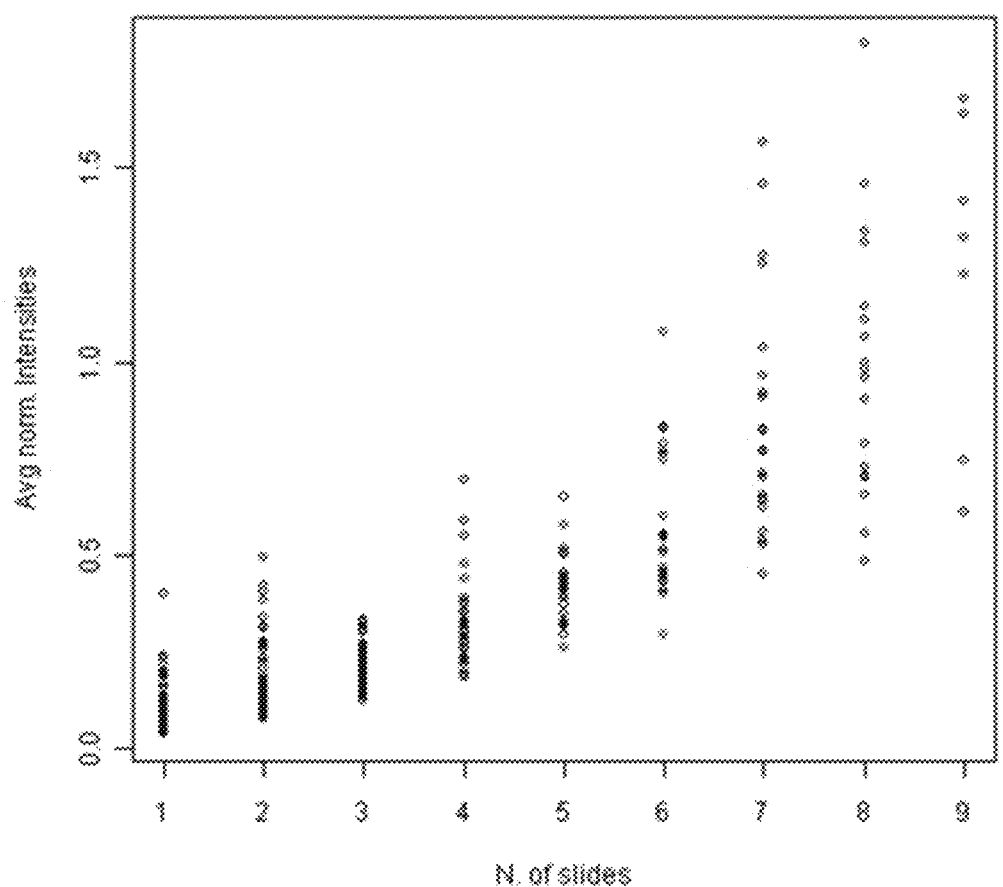
FIG. 4A shows antibody recognition of glycosyltransferase in individuals with sarcoidosis (SRC).
Figure 4B:
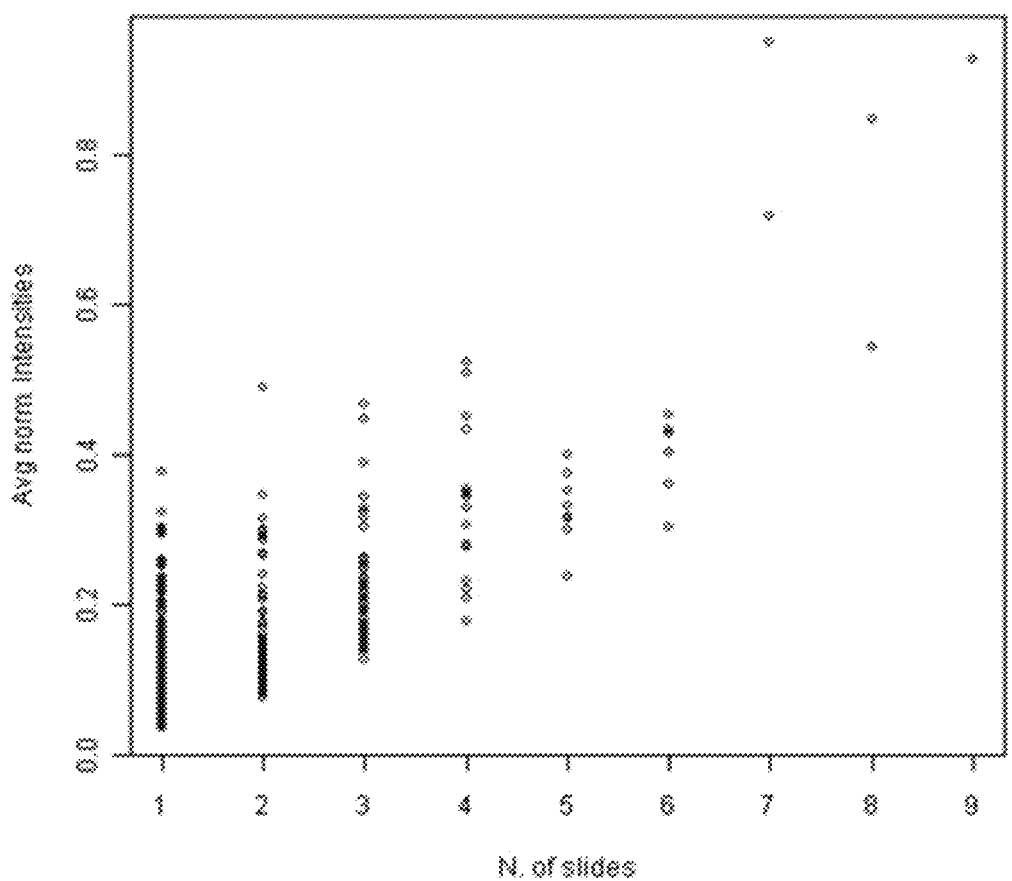
FIG. 4B shows antibody recognition of glycosyltransferase in individuals with TB.

Example 4. Antibody Recognition of Glycosyltransferase CAB05419 in Individuals with TB Serum was obtained from patients with sarcoidosis (FIG. 4A) and from patients with TB (FIG. 4B). The number indicate the frequency of recognition, e.g. 1/9 individuals up to 9/9 individuals. The listed peptides are only listed if they are present in one group (sarcoidosis versus tuberculosis) and if the peptide is never recognized in any serum from the respective control group. Note that glycosyltransferase CAB05419 represents the top epitope which is most frequently recognized, with the highest intensity and never in the control (sarcoidosis group). Strong IgG response requires strong T-cell help which lends support that these antigens are also recognized by T-cells.

TABLE 8a

Peptides present and recognized with the highest intensity by serum from the group sarcoidosis and never from the group TB

| Peptide | Average int. | N. of slide | Proteins |
|---|---|---|---|
| APALMDVEAAYEQMW | 1.6787 | 9 | CAE55281-PPE family protein_133 |
| LSGDNQQGFNFAGGW | 1.6435 | 9 | CAE55276-PPE family protein_1117 |
| NANFGGGNGSAFHGQ | 1.4131 | 9 | CAE55320-PPE family protein_205 |
| SSGKPGRDPEAGRYG | 1.3190 | 9 | CAB02482-probable lipase lipe_385 |
| GGGNTGSGNIGNGNK | 1.2266 | 9 | CAE55613-PPE family protein_193 |
| VIGGIGPIHVQPIDI | 0.7433 | 9 | CAE55585-PPE family protein_865 |
| GSSAMILAAYHPQQF | 0.6077 | 9 | CAB10044-secreted antigen 85-B FBPB (85B)A_169 |

TABLE 8b

Peptides present and recognized with the highest intensity by serum from the group TB and never from the group sarcoidosis

| Peptide | Average int. | N. of slide | Proteins |
|---|---|---|---|
| TRLGIRLV IVLVRRW | 0.92644 | 9 | CAB05419-possible glycosyl transferase_241 |
| MTAPVWLA SPPEVHS | 0.84613 | 8 | CAE55538-PPE family protein_1 |

TABLE 8b -continued

Peptides present and recognized with the highest intensity by serum from the group TB and never from the group sarcoidosis

| Peptide | Average int. | N. of slide | Proteins |
|---|---|---|---|
| GLYQVVPG IYQVRGF | 0.54323 | 8 | CAA18084-possible hydrolase_85 |
| NTGSYNMG DFNPGSS | 0.94791 | 7 | CAE55416-PPE family protein_385 |
| AWVSRGAH KLVGALE | 0.71754 | 7 | CAB10951-cytotoxin haemolysin homologue TLYA_61 |
| AAGNNVTV FGYSQSA | 0.45450 | 6 | CAE55427-PPE family protein_289 |
| QWILHMAK LSAAMAK | 0.43328 | 6 | CAA17973-conserved hypothetical alanine and_193 |

Example 5. Detection of IFNγ in Response to Peptide Pools from Different *M. tuberculosis* Target Antigens Note that 'healthy individuals' have been exposed to *M. tuberculosis*, they are protected from TB. Note that the peptide pools do not cover the entire target proteins, the results are therefore underestimated.

TABLE 9

Detection of IFNγ in response to peptide pools from different *M. tuberculosis* target antigens

| Peptide pools | Healthy (n = 15) (%) | Previous TB n = 15 (%) | TB+ patients n = 15 (%) |
|---|---|---|---|
| Rv0447c | 4 (27) | 11 (73) | 7 (47) |
| Rv2957 | 7 (47) | 9 (60) | 4 (27) |
| Rv1085c | 5 (33) | 7 (47) | 5 (33) |
| Rv0066c | 8 (53) | 6 (40) | 4 (27) |
| Rv2958c | 8 (53) | 4 (27) | 3 (20) |
| Rv2962 | 5 (33) | 6 (40) | 3 (20) |

Example 6: Detection of IFNγ Production in Freshly Harvested Heparin-Blood from Individuals Cured from MDR or XDR TB by Autologous Mesenchymal Stem Cells (MSCs)

Figure 5:
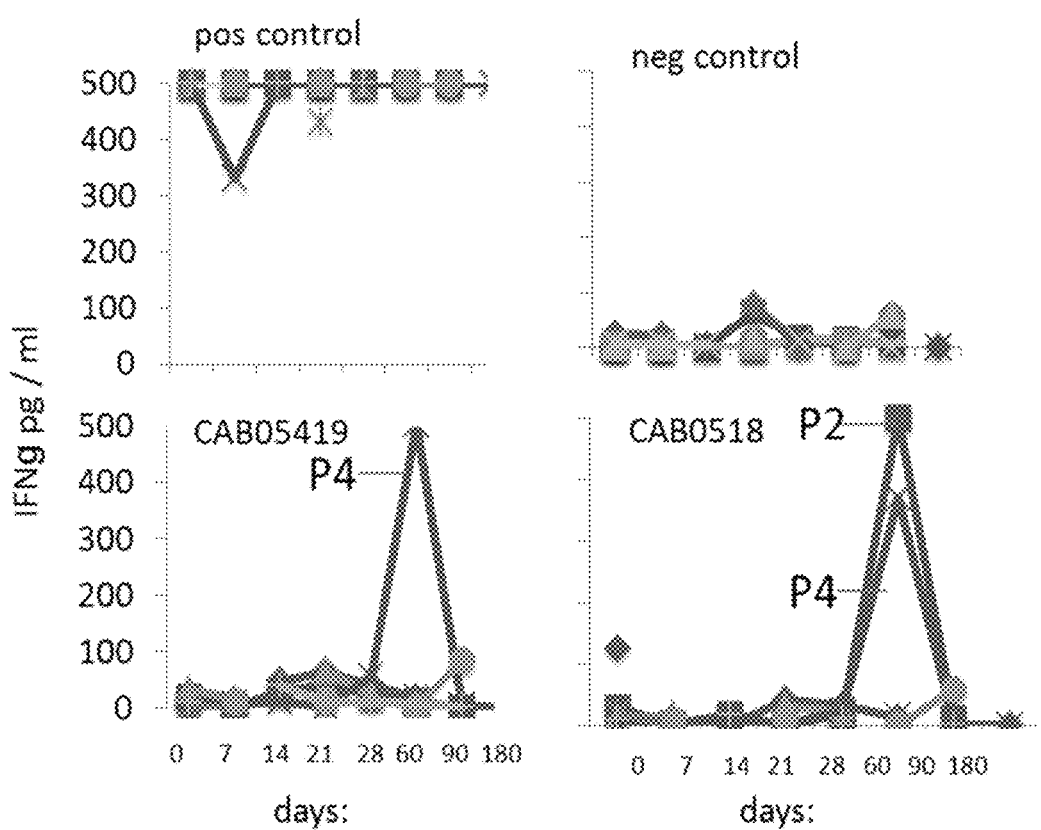
FIG. 5 shows detection of IFNγ production in freshly harvested Heparin-blood from individuals cured from MDR or XDR TB by infusion of autologous mesenchymal stem cells (MSCs). The patients regained reactivity to the antigens, defined by IFNγ production.

Results are presented in FIG. 5.
Note that reactivity to Rv2957 and Rv2958c occurs in individuals who were able to effectively fight off *M. tuberculosis*. Top panel; left. pos control; Individuals suffered from MDR (multidrug resistant) and XDR (extensive multidrug resistant) TB—and failed at least one treatment regimen. These individuals were enrolled in a new treatment protocol using autologous mesenchymal stem cells (MSCs). Note that antigen-specific T-cell responses are absent (defined by INFy responses), yet Rv2957/Rv2958c specific T-cell responses can be detected approximately 60 days after MSC infusion and this correlated with response to therapy.

Figure 14:
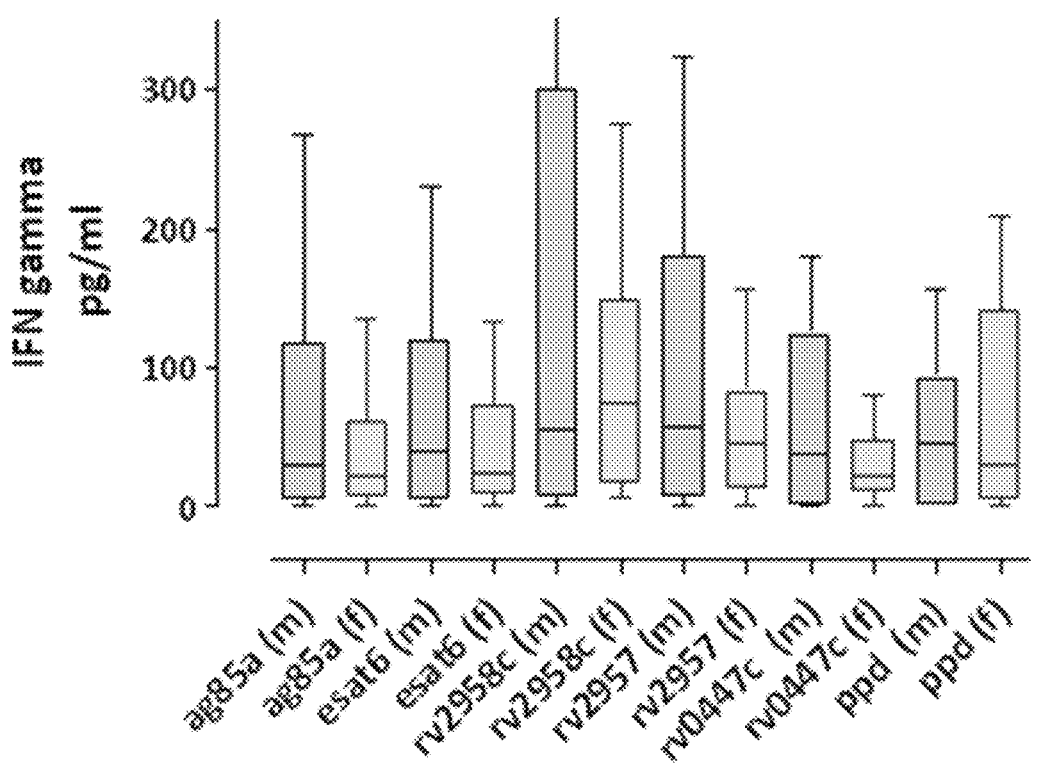
FIG. 14 shows the IFNγ production in whole blood samples obtained from patients with active TB in response to different *M. tuberculosis* antigens. Fresh heparin blood was obtained from patients with active TB (n=50) and tested for IFNγ production using a whole-blood assay. Note a strong IFNγ production directed against the CAB05418/Rv2958c antigen. (m) male patient, (f) female patients.

Example 7. IFNγ Production in Whole Blood Samples Obtained from Patients with Active TB in Response to Different *M. tuberculosis* Antigens Results are presented in FIG. 14.
Fresh heparin blood was obtained from patients with active TB (n=50) and tested for IFNγ production using a whole-blood assay. Note a strong IFNγ production directed against the CAB05418/Rv2958c antigen.

Figure 15:
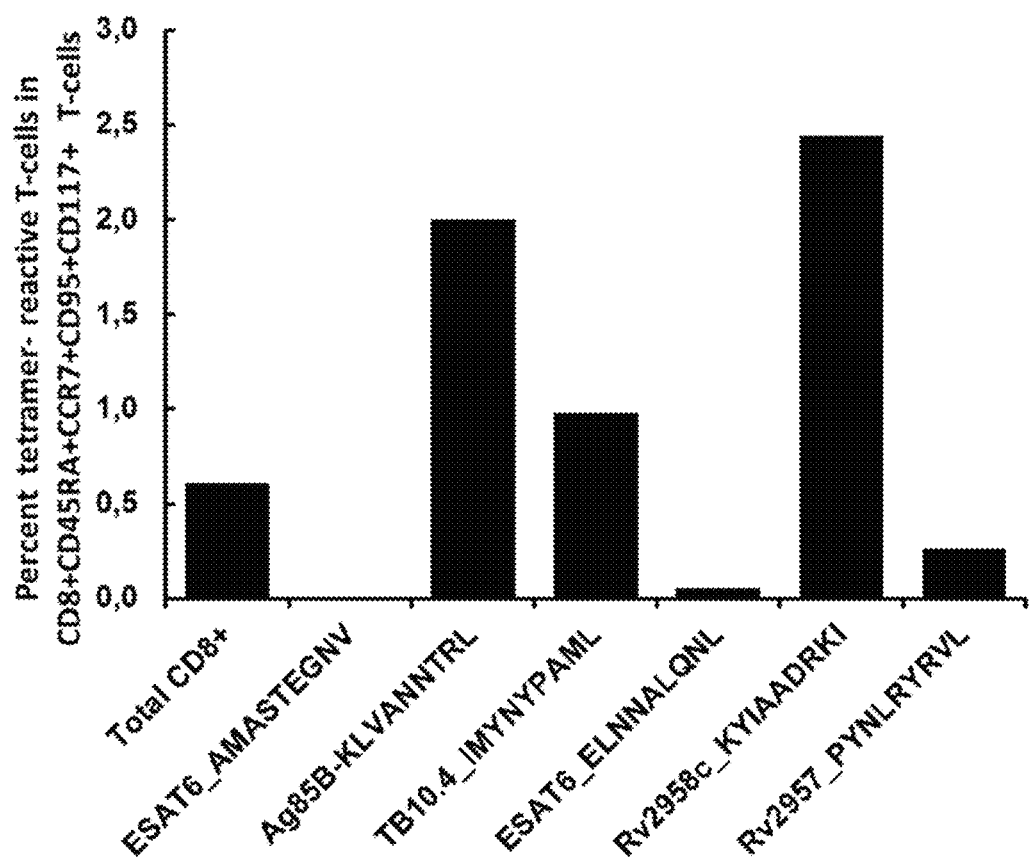
FIG. 15 shows the percentage of tetramer-reactive CD8+ CD45RA+ CCR7+ CD117+ CD95+ T-cells recognizing specific peptides from different *M. tuberculosis* antigens.

Example 8: Anti-CAB05418/Rv2958c Specific T-Cell Responses Reside in the Precursor Memory T-Cell Pool with Stem-Cell Like Features Results are presented in FIG. 15.
Blood from patients with active TB was obtained and tested for target antigen-specific recognition using tetramer-based staining and immune marker analysis. CD45RA/CCR7 enables to define whether a T-cell reside in the precursor (CD45RA+CCR7+), in the memory (CD45RA−CCR7+ or CD45RA−CCR7−) or in the terminally differentiated effector T-cell pool (CD45RA+CCR7−). Staining with CD95 and CD117 (ckit) can identify T-cells with stem cell-like features. Note that T-cell reacting to a peptide, presented by HLA-A*2402, from CAB05418/Rv2958c showed the highest percentage in CD8+ T-cells exhibiting stem-cell like features.

Example 9. Biology of the *M. tuberculosis* Vaccine Candidates—Rationally Based Design of New Vaccines The three *M. tuberculosis* candidate vaccines according to the invention CAB05419/Rv2957; CAB05418/Rv2958 and CAA17404/Rv0477c were expressed as recombinant proteins in an *E. coli* expression system, followed by an LPS removal procedure. The final LPS content was below the EU Standard for clinical material.

Figure 6:
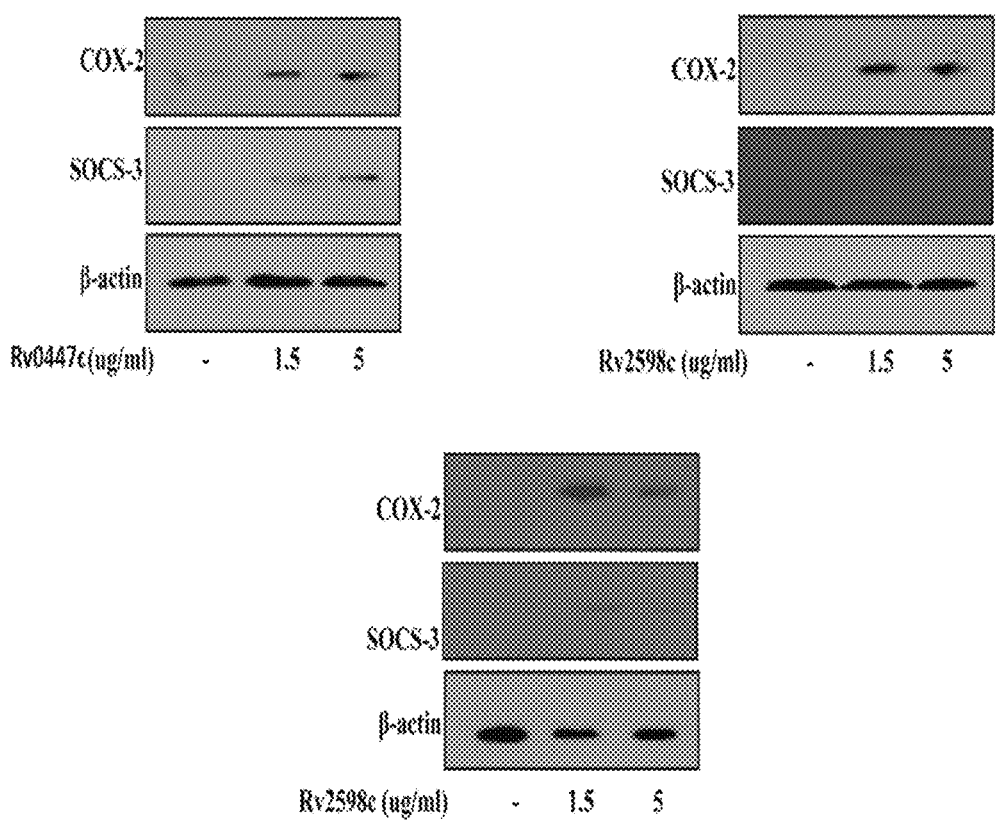
FIG. 6 shows detection of COX-2 and SOCS-3 protein expression by Western Blot analysis in mouse peritoneal macrophages stimulated with the CAB05419/Rv2957; CAB05418/Rv2958c and CAA17404/Rv0477c antigens.
Figure 7:
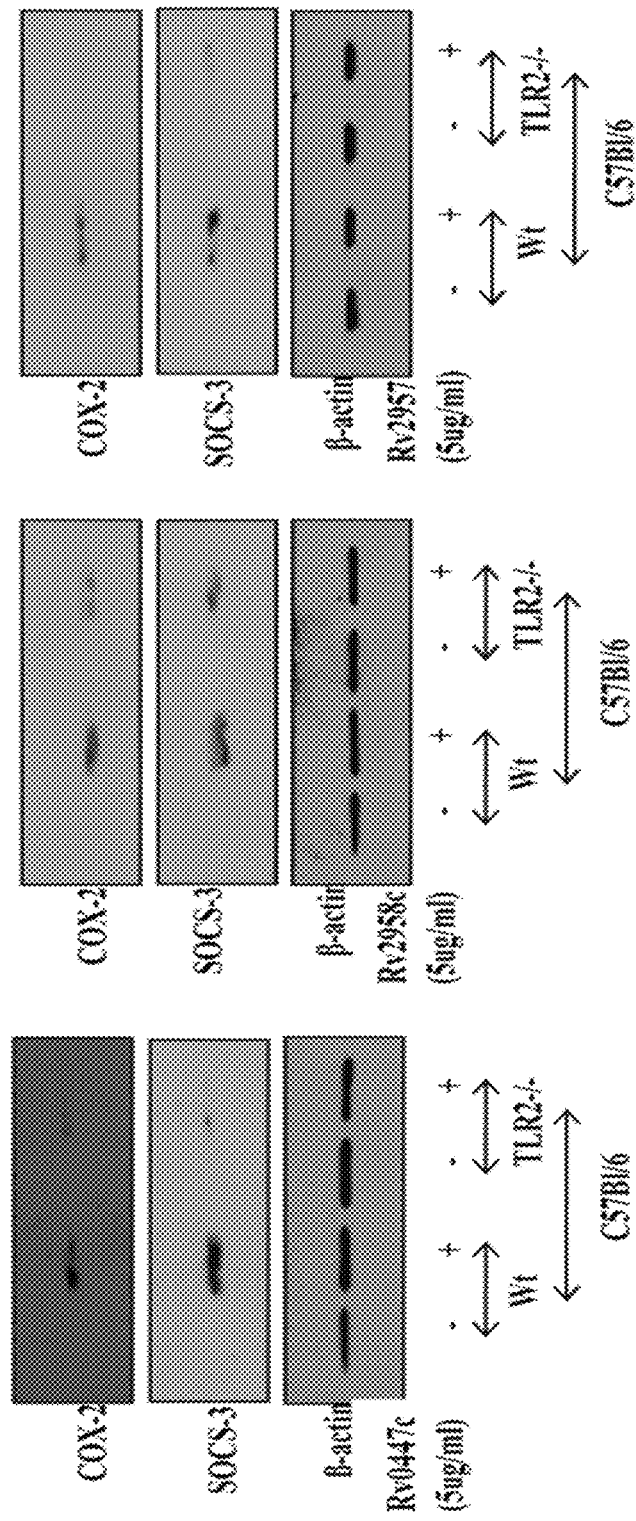
FIG. 7 shows detection of COX-2 and SOCS-3 protein expression by Western Blot analysis in mouse peritoneal macrophages obtained from TLR knock-out mice stimulated with the CAB05419/Rv2957; CAB05418/Rv2958c and CAA17404/Rv0477c antigens.
Figure 8:
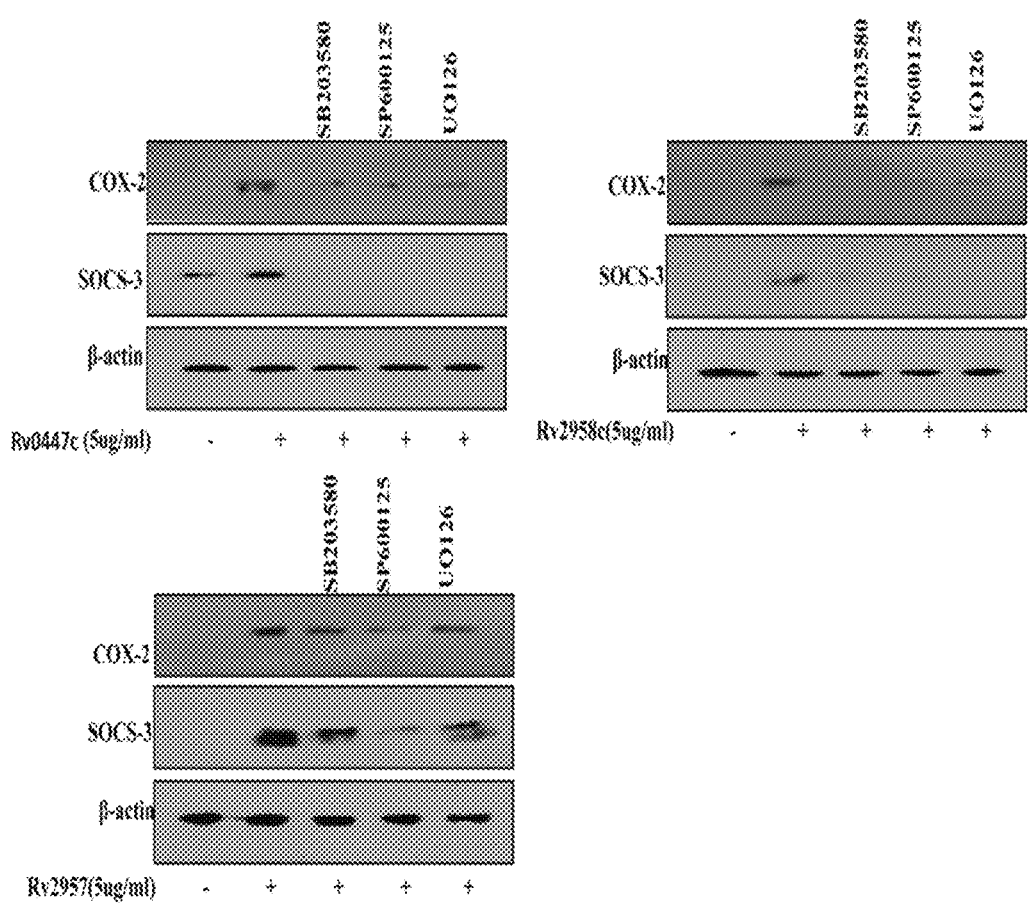
FIG. 8 shows the effect of MAP kinase inhibitors on COX-2 and SOCS-3 protein expression in mouse peritoneal macrophages stimulated with the CAB05419/Rv2957; CAB05418/Rv2958c and CAA17404/Rv0477c antigens.
Figure 9:
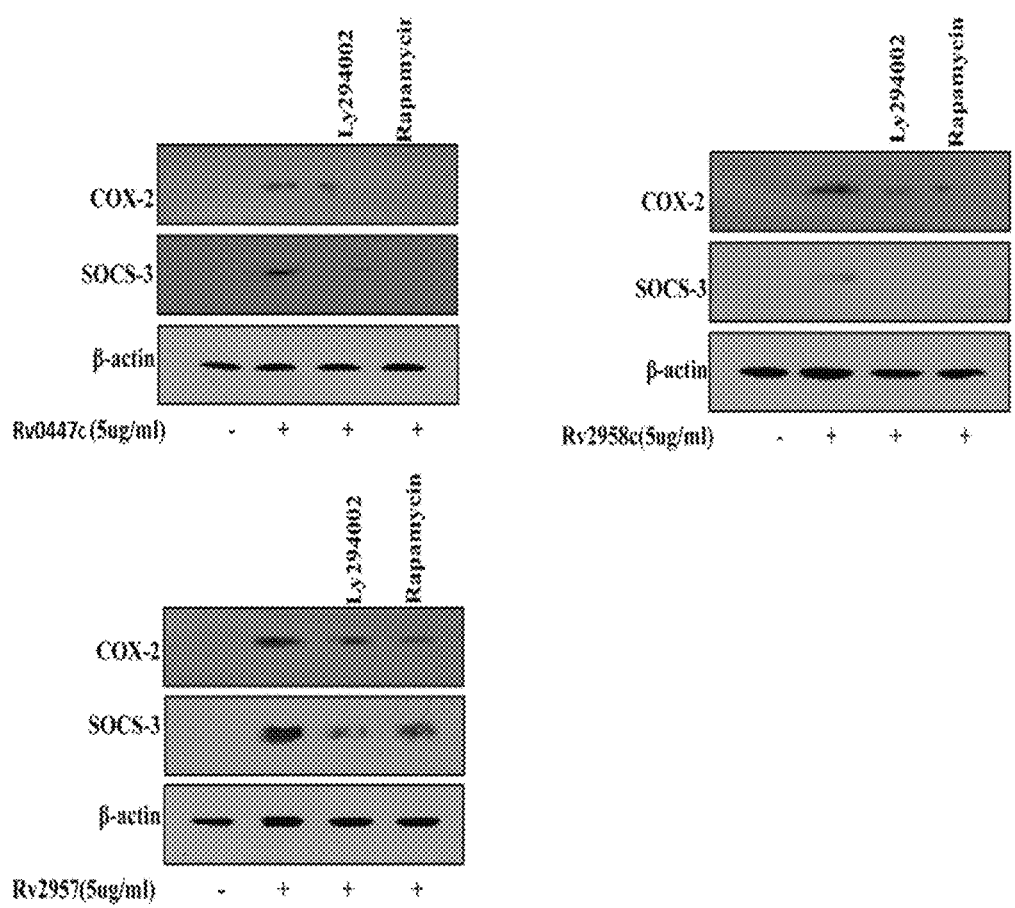
FIG. 9 shows the effect of PI3 kinase and mTOR inhibitors on COX-2 and SOCS-3 protein expression in mouse peritoneal macrophages stimulated with the CAB05419/Rv2957; CAB05418/Rv2958c and CAA17404/Rv0477c antigens.
Figure 10:
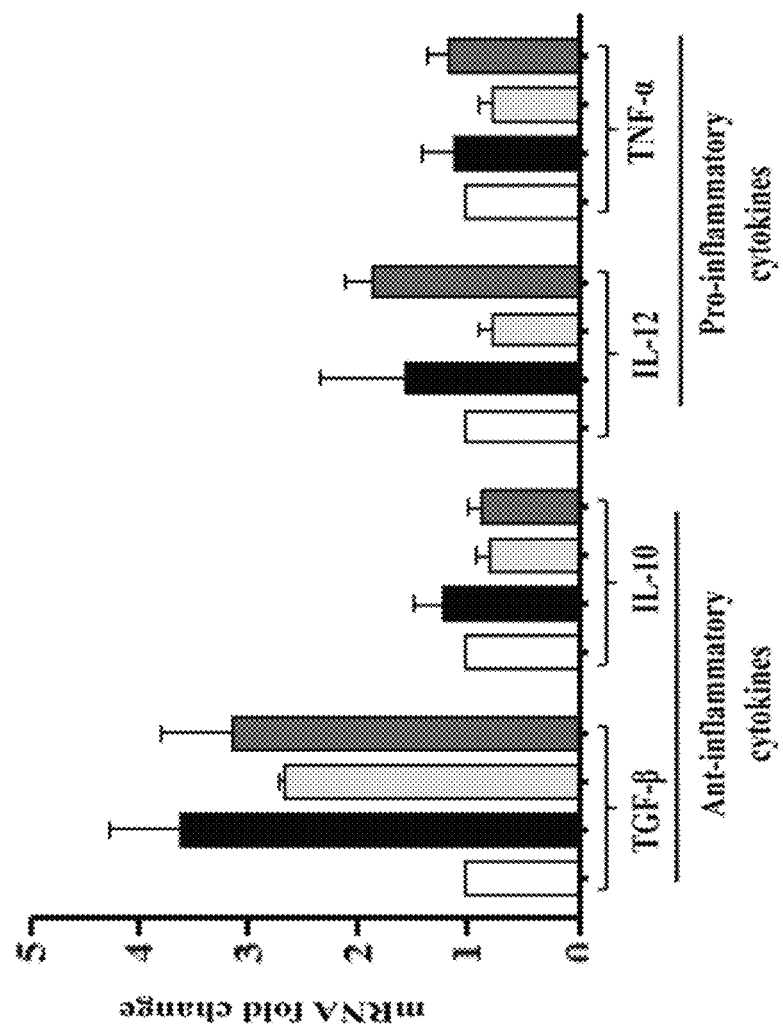
FIG. 10 shows the induction of TGF-β, IL-10, IL-12 and TNF-α in peritoneal macrophages stimulated by the CAB05419/Rv2957; CAB05418/Rv2958 and CAA17404/Rv0477c antigens. (order of bars: control, —CAA17404/Rv0477c, —CAB05418/Rv2958c, —CAB05419/Rv2957.

Each protein was tested for immune-reactivity in murine models for *M. tuberculosis* antigen biology.
A. Mouse peritoneal macrophages were obtained and exposed to different concentrations of the test antigens, COX-2 and SOCS-3 protein expression was tested by Western Blot analysis. Beta-actin served as the positive control for equal amount of sample loading. Induction of COX-2 and SOCS-3 in a dose-dependent manner was observed (FIG. 6.).
B. The experiments were repeated using macrophages harvested from TLR2 knockout mice. Only cells from TLR2+ animals show induction of COX-2 and SOCS-3 mediated by the Test antigens, (FIG. 7) suggesting that signaling occurs via TLR2.
C. Different MAP kinase inhibitors (MEK1/2 inhibitor UO126, p38 inhibitor SB203580 and JNK inhibitor SP600125) were used to interfere with COX2 and SOCS-3 expression. (FIG. 8). At least CAB05418/Rv02958 and CAA17404/Rv0477c mediate COX2 expression and SOCS-3 via the MAP kinase pathway.
D. PI3 kinase (LY294002) and mTOR (rapamycin) inhibitors were tested. (FIG. 9). At least CAB05418/Rv02958 and CAA17404/Rv0477c mediate COX2 expression and SOCS-3 via PI3 kinase and the mTOR pathway.
E. Peritoneal macrophages were stimulated with the candidate antigens. Strong induction of TGF-β and IL-12 by CAB05419/Rv02957 and CAA17404/Rv0477c, yet little induction of IL-10 and TN-Fa, was observed (FIG. 10, order of bars—control, CAA17404/Rv0477c, —CAB05418/Rv2958, —CAB05419/Rv2957). This is a very interesting cytokine induction pattern; since both anti-inflammatory (TGF-β) and pro-inflammatory (IL-12) cytokines are produced. Note that, dependent on the presence of other cytokines, TGF-β can give rise to either regulatory T-cells (Treg) or to pro-inflammatory T-cells of the Th17 type (production of IL-17 attracting neutrophils to the site of inflammation).

Figure 11:
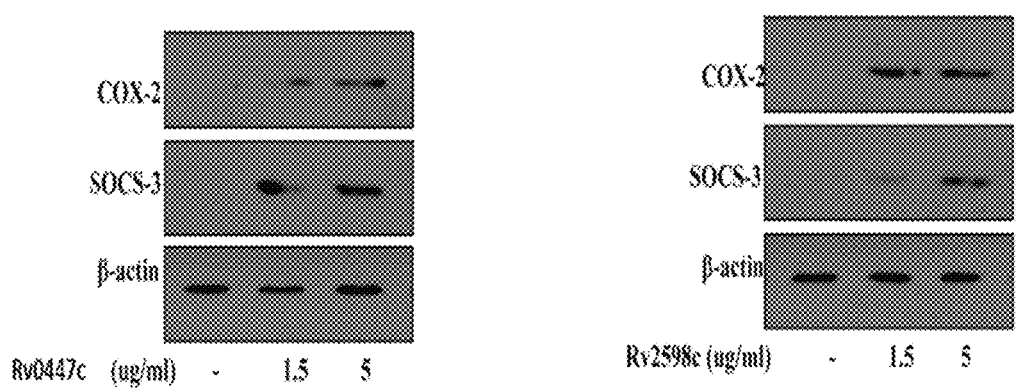
FIG. 11 shows detection of COX-2 and SOCS-3 protein expression by Western Blot analysis in the human monocyte cell line (THP1) stimulated with the CAB05419/Rv2957; CAB05418/Rv2958 and CAA17404/Rv0477c antigens.
Figure 11:
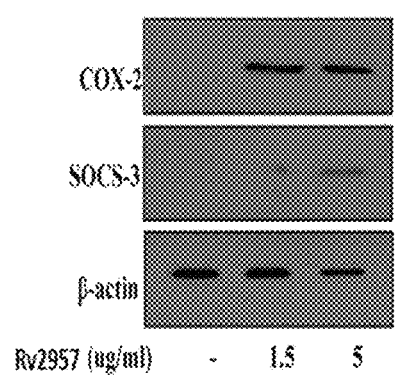

F. The experiments performed under A) were repeated using the human monocyte cell line (THP1): Induction of COX2 and SOCS-3 by can be seen by all three antigens (FIG. 11).

Figure 12:
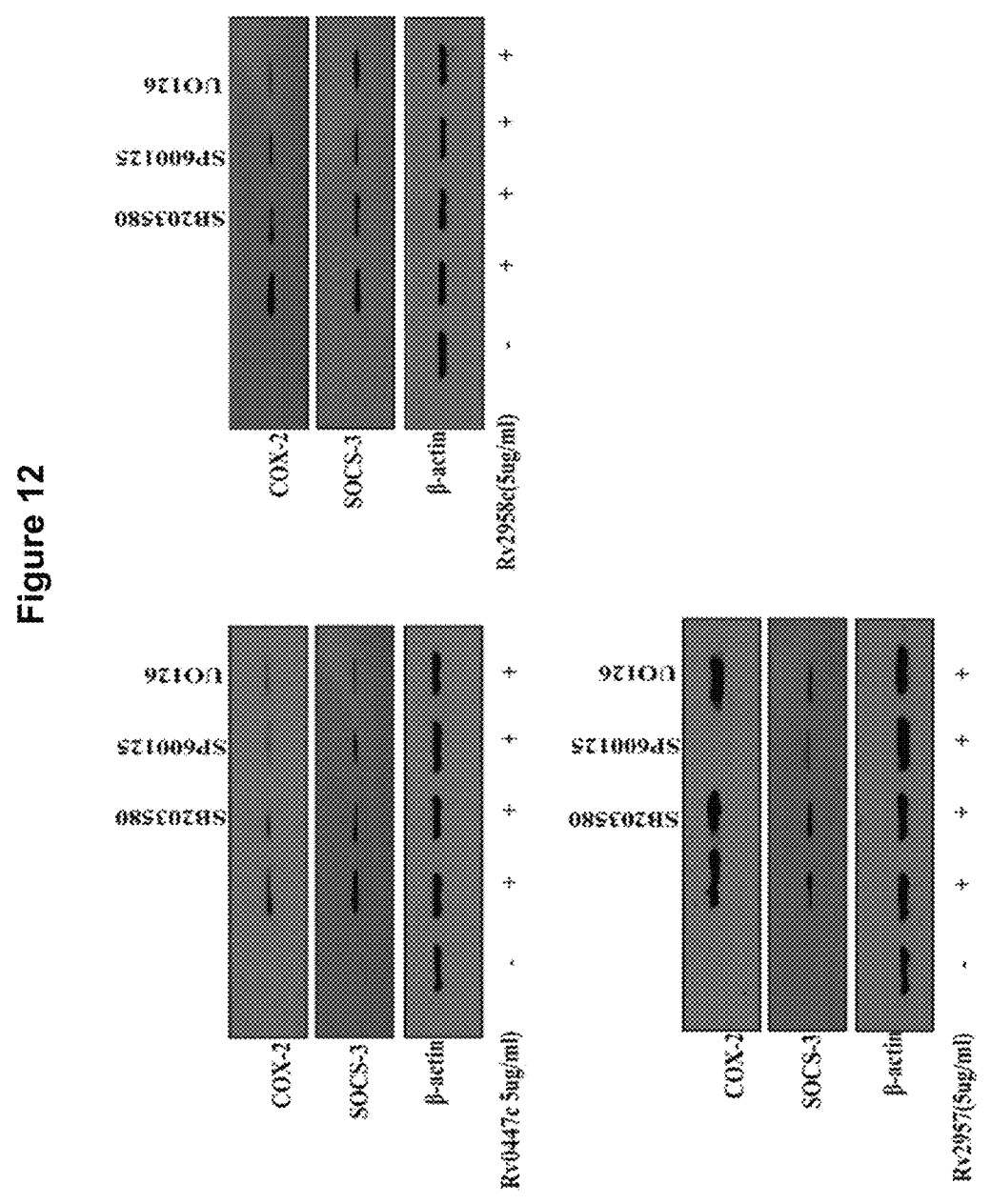

G. Possible role of the MAP kinases was in THP1 cells using the same experimental setup as in experiment C) above. Results in FIG. 12.

Figure 13:
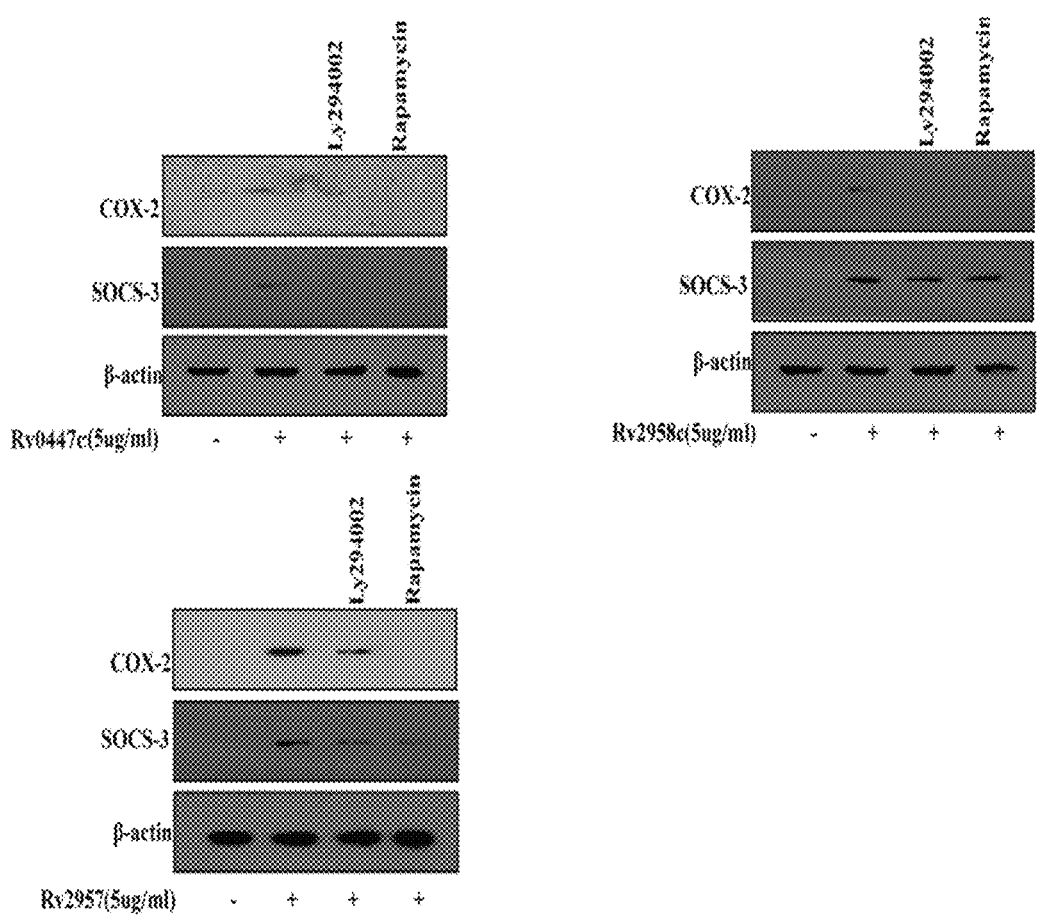
FIG. 13 shows the effect of PI3 kinase and mTOR inhibitors on COX-2 and SOCS-3 protein expression in human monocyte cell line (THP1) stimulated with the CAB05419/Rv2957; CAB05418/Rv2958c and CAA17404/Rv0477c antigens.

H. The role of mTOR and PI3 in COX2 and SOCS-3 protein expression in the defined monocyte cell line THP1 induced by the candidate antigens was studied in accordance with experiment D) above. Results in FIG. 13.

CONCLUSIONS

The Mycobacterial antigens according to the invention CAA17404/Rv04417c, CAB05418/Rv2958c and CAB05419/Rv2957 induce expression of COX-2 and SOCS-3 in macrophages.

Induced expression of COX-2 and SOCS-3 by mycobacterial antigens is dependent on pattern recognition receptors like Toll Like receptor-2.

TLR-2 dependent expression of COX-2 and SOCS-3 by mycobacterial proteins is regulated by MAPkinases (ERK1/2, SAPK/JNK and p38) and PI3 Kinase pathway in macrophages.

The Mycobacterial antigens according to the invention CAA17404/Rv04417c, CAB05418/Rv2958c and CAB05419/Rv2957 induced expression of anti-inflammatory cytokines and immune-regulatory cytokines like TGF-β (predominantly) over pro-inflammatory cytokine like IL-12 and TNF-α. TGFβ may not only induce immunoregulatory T-cells (Treg), yet also Th17 cells which may, depending on the stage of infection/exposure history), represent biologically and clinically relevant anti-*M. tuberculosis* directed T-cells. The induction of TGFβ along with the pro-inflammatory cytokine IL-12, in addition to other cytokines elaborated at the site of infection/vaccination may also drive the development of Th17 cells. Anti-CAB05418/Rv2958c directed T-cells reside in a precursor T-cell compartment with 'stem-cell-like-features—(CD95+, CD117, c-kit+). These T-cells may be truly 'naïve' or they may present antigen-experienced T-cells which reside in a particular memory T-cell pool that is long-lived. A long-lived memory T-cell response is advantageous for long-term memory immune responses.

The invention claimed is:

1. A method of eliciting an immune response against *Mycobacterium tuberculosis* in a mammalian subject comprising the step of administering to said subject an immunological composition consisting essentially of a first isolated polypeptide of the amino acid sequence of SEQ ID NO: 1, a second isolated polypeptide of the amino acid sequence of SEQ ID NO: 2, and a third isolated polypeptide of the amino acid sequence of SEQ ID NO: 3 and at least one of a pharmaceutically acceptable carrier and an adjuvant.

2. The method of claim 1, wherein the immunological composition is formulated for administration via different routes.

* * * * *